United States Patent
Matsuura

(10) Patent No.: US 9,895,132 B2
(45) Date of Patent: Feb. 20, 2018

(54) MAMMOGRAPHY APPARATUS, CONTROL DEVICE, CONTROL METHOD FOR MAMMOGRAPHY APPARATUS, AND PROGRAM STORAGE MEDIUM

(71) Applicant: FUJIFILM CORPORATION, Tokyo (JP)

(72) Inventor: Masayoshi Matsuura, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 42 days.

(21) Appl. No.: 14/936,689

(22) Filed: Nov. 10, 2015

(65) Prior Publication Data
US 2016/0183889 A1    Jun. 30, 2016

(30) Foreign Application Priority Data
Dec. 26, 2014 (JP) .................................. 2014-266485

(51) Int. Cl.
*A61B 6/04* (2006.01)
*A61B 6/00* (2006.01)

(52) U.S. Cl.
CPC .............. *A61B 6/54* (2013.01); *A61B 6/0414* (2013.01); *A61B 6/502* (2013.01)

(58) Field of Classification Search
CPC .............. A61B 6/502; A61B 2090/036; A61B 2562/164; A61B 2090/3908
USPC ........................... 378/37, 177, 179, 195, 208
See application file for complete search history.

(56) References Cited

U.S. PATENT DOCUMENTS

| | | | |
|---|---|---|---|
| 6,999,553 B2* | 2/2006 | Livingston | A61B 6/502 378/177 |
| 2005/0008117 A1 | 1/2005 | Livingston | |
| 2006/0126794 A1 | 6/2006 | Harmann et al. | |
| 2013/0129039 A1* | 5/2013 | DeFreitas | A61B 6/04 378/37 |
| 2016/0051207 A1* | 2/2016 | Timberg | A61B 6/0414 378/62 |

FOREIGN PATENT DOCUMENTS

| | | |
|---|---|---|
| JP | 2008-513090 A | 5/2008 |
| JP | 2008-518722 A | 6/2008 |
| JP | 2013-013775 A | 1/2013 |

OTHER PUBLICATIONS

English Language translation of the following: Office Action dated Nov. 21, 2017 from the JPO in a Japanese patent application No. 2014-266485 corresponding to the instant patent application. This office action translation is submitted now in order to supplement the understanding of the cited reference which is being disclosed in the instant information Disclosure Statement.

* cited by examiner

*Primary Examiner* — Don Wong
(74) *Attorney, Agent, or Firm* — SOLARIS Intellectual Property Group, PLLC

(57) ABSTRACT

A mammography apparatus includes: an imaging table housing a radiation detector that detects radiation that has passed through a breast of a subject; a first press member that presses the breast downward from above in a case in which radiation is being detected by the radiation detector; and a second press member that is provided facing the first press member and that presses the breast upward from below, wherein an end portion of the second press member at a chest wall side of the subject is supported by the imaging table.

13 Claims, 19 Drawing Sheets excellent# MAMMOGRAPHY APPARATUS, CONTROL DEVICE, CONTROL METHOD FOR MAMMOGRAPHY APPARATUS, AND PROGRAM STORAGE MEDIUM

CROSS-REFERENCE TO RELATED APPLICATION

This application claims priority under 35 USC 119 from Japanese Patent Application No. 2014-266485, filed on Dec. 26, 2014, the disclosure of which is incorporated by reference herein.

BACKGROUND

Field of the Art

The present disclosure relates to a mammography apparatus, control device, and mammography apparatus control method, and program storage medium.

Related Art

A mammography apparatus is known that captures radiographic images of a breast of a subject. During imaging of the breast of the subject using the mammography apparatus, the breast is fixed using a press plate.

Generally, when a breast is fixed by a press plate, often the subject feels pain due to the breast being stretched and strongly pressed, with this being a burden on the subject.

Therefore, the technology described in, for example, Japanese Patent Application Laid-Open (JP-A) No. 2013-013775 and Japanese National Publication No. 2008-513090 is known as conventional technology to reduce the burden on a subject.

JP-A No. 2013-013775 describes technology in which a gel pad is provided for one of, or both of, a press plate or a bucky. Japanese National Publication No. 2008-513090 describes technology in which at least a portion surrounding the breast is packed with a soft band.

However, since the way in which pain is experienced is not uniform and differs depending on the subject, depending on the firmness of the breast of the subject, the above conventional technology is not always able to effectively reduce the pain of a subject.

SUMMARY

The present disclosure provides a mammography apparatus, a control device, a mammography apparatus control method, and a program storage medium capable of effectively reducing pain in a breast due to pressing.

A first aspect of the present disclosure is a mammography apparatus including: an imaging table housing a radiation detector that detects radiation that has passed through a breast of a subject; a first press member that presses the breast downward from above in a case in which radiation is being detected by the radiation detector; and a second press member that is provided facing the first press member and that presses the breast upward from below, wherein an end portion of the second press member at a chest wall side of the subject is supported by the imaging table.

The first aspect may be configured such that an end portion of the second press member at the far side that is opposite to the end portion at the chest wall side is moved in a direction separating away from the imaging table in a case in which the breast is being pressed by the second press member.

The first aspect may further include a control section that is configured to effect control of setting a first pressing pressure for pressing the breast with the first press member and a second pressing pressure for pressing the breast with the second press member, based on at least two factors selected from the group of: a detected pressing pressure of the first press member pressing the breast; a contact surface area of the breast with at least one of the first press member or the second press member; and a movement amount that at least one of the first press member or the second press member has moved to press the breast.

The first aspect may be configured such that the control section is configured to set the first pressing pressure and the second pressing pressure so as to give different relative proportions of the first pressing pressure and the second pressing pressure, based on a determination result determining whether or not the movement amount corresponding to the detected pressing pressure is less than a first threshold value.

The first aspect may be configured such that the control section is configured to set the first pressing pressure and the second pressing pressure so as to give different relative proportions of the first pressing pressure and the second pressing pressure, based on a determination result determining whether or not an amount of change in the contact surface area, over a period up to a movement amount of the first press member reaches a predetermined movement amount, is larger than a predetermined second threshold value that has been set according to a predetermined firmness.

The first aspect may be configured such that the control section is configured to set the first pressing pressure and the second pressing pressure so as to give different relative proportions of the first pressing pressure and the second pressing pressure, based on a determination result that determines whether or not an amount of change in the contact surface area, over a period up to the detected pressing pressure due to movement of the first press member has reached a predetermined pressing pressure, is larger than a predetermined third threshold value that has been set according to the predetermined firmness.

The first aspect may be configured such that the control section is configured to effect control of setting the second pressing pressure to be larger than the first pressing pressure, or effect control of moving only the second press member, in a case in which it is determined that the movement amount corresponding to the detected pressing pressure is less than the first threshold value.

The first aspect may be configured such that the control section is configured to effect control of setting the second pressing pressure to be larger than the first pressing pressure, or effect control of moving only the second press member, in a case in which it is determined that the amount of change in the contact surface area is larger than the second threshold value.

The first aspect may be configured such that the control section is configured to effect control of setting the second pressing pressure to be larger than the first pressing pressure, or effect control of moving only the second press member, in a case in which it is determined that the amount of change in contact surface area is larger than the third threshold value.

The first aspect may be configured such that the second press member is supported by the imaging table so as to be capable of swinging, or is supported by being fixed.

In the first aspect, the second press member may be a film-shaped member.

A second aspect of the present disclosure is a control device for controlling a mammography apparatus including an imaging table housing a radiation detector that detects radiation that has passed through the breast of a subject, a first press member that presses the breast downward from above in a case in which radiation is being detected by the radiation detector, and a second press member that is provided facing the first press member and that presses the breast upward from below, wherein an end portion of the second press member at a chest wall side of the subject is supported by the imaging table, the control device including a control section that is configured to effect control of setting a first pressing pressure for pressing the breast with the first press member and a second pressing pressure for pressing the breast with the second press member, based on at least two factors selected from the group of: a detected pressing pressure of the first press member pressing the breast; a contact surface area of the breast with at least one of the first press member or the second press member; and a movement amount moved by at least one of the first press member or the second press member to press the breast.

The second aspect may be configured such that the control section is configured to effect control of setting the second pressing pressure to be larger than the first pressing pressure.

A third aspect of the present disclosure is a control method of a mammography apparatus including an imaging table housing a radiation detector that detects radiation that has passed through the breast of a subject, a first press member that presses the breast downward from above in a case in which radiation is being detected by the radiation detector, and a second press member that is provided facing the first press member and that presses the breast upward from below, wherein an end portion of the second press member at a chest wall side of the subject is supported by the imaging table, the control method causing a computer to execute processing including: setting a first pressing pressure for pressing the breast with the first press member and a second pressing pressure for pressing the breast with the second press member, based on at least two factors selected from the group of: a detected pressing pressure of the first press member pressing the breast; a contact surface area of the breast with at least one of the first press member or the second press member; and a movement amount that at least one of the first press member or the second press member has moved by to press the breast.

A fourth aspect of the present disclosure is a non-transitory storage medium storing a program that causes a computer to execute control processing of a mammography apparatus including an imaging table housing a radiation detector that detects radiation that has passed through the breast of a subject, a first press member that presses the breast downward from above in a case in which radiation is being detected by the radiation detector, and a second press member that is provided facing toward the first press member and that presses the breast upward from below, wherein an end portion of the second press member at a chest wall side of the subject is supported by the imaging table, the control processing including: setting a first pressing pressure for pressing the breast with the first press member and a second pressing pressure for pressing the breast with the second press member, based on at least two factors selected from the group of: a detected pressing pressure of the first press member pressing the breast; a contact surface area of the breast with at least one of the first press member or the second press member; and a movement amount that at least one of the first press member or the second press member has moved by to press the breast.

The present disclosure enables pain in a breast due to pressing to be effectively reduced.

BRIEF DESCRIPTION OF THE DRAWINGS

Exemplary embodiments will be described in detail based on the following figures, wherein.

DETAILED DESCRIPTION

Detailed explanation follows regarding exemplary embodiments of the present disclosure, with reference to the drawings. The present exemplary embodiments do not limit the present disclosure.

First Exemplary Embodiment

Figure 1:
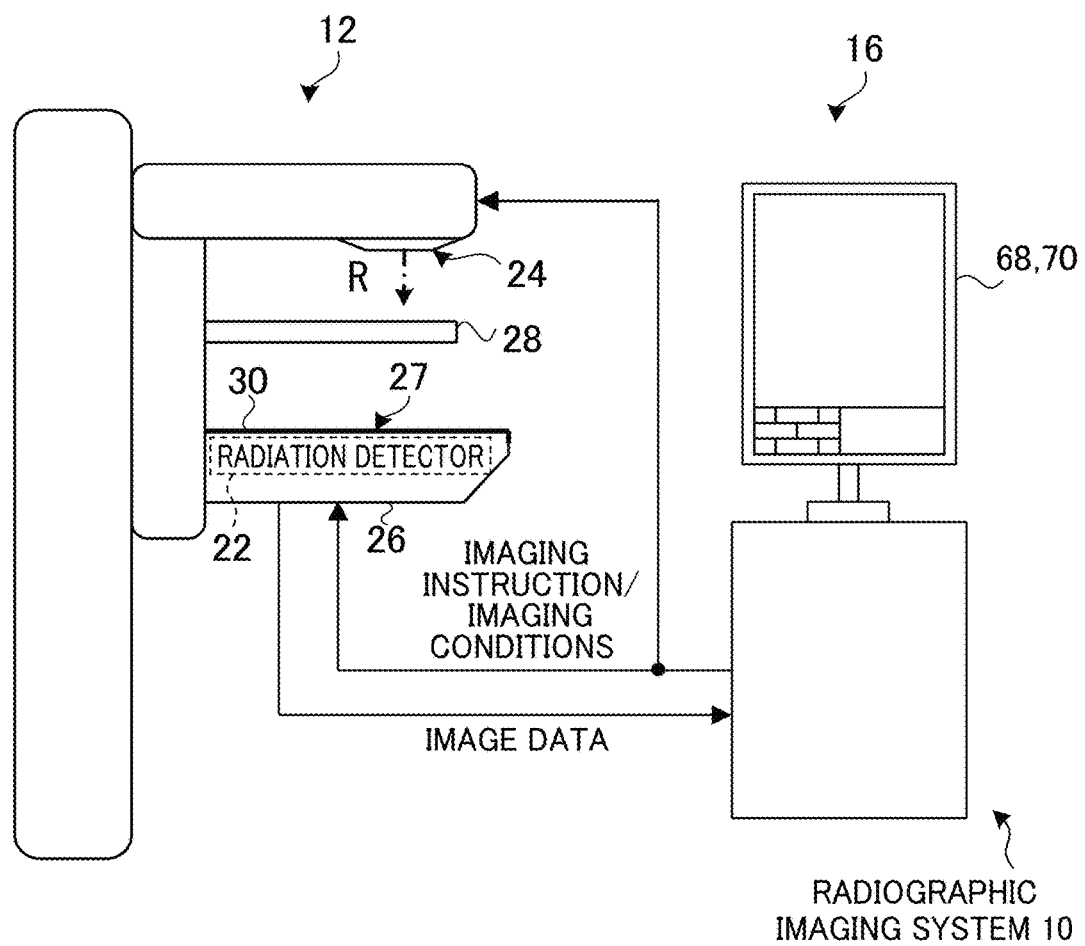
FIG. 1 is a configuration diagram of a radiographic imaging system of an exemplary embodiment.

Explanation first follows regarding an overall configuration of a radiographic imaging system of the present exemplary embodiment. FIG. 1 is a configuration diagram illustrating a radiographic imaging system 10 of the present exemplary embodiment.

The radiographic imaging system 10 captures radiographic images under operation by a user, such as a doctor or radiographer, based on instructions (an imaging menu) input from an external system (for example, a Radiology Information System (RIS)) through a console 16.

The radiographic imaging system 10 of the present exemplary embodiment includes a mammography apparatus 12, and the console 16.

The mammography apparatus 12 of the present exemplary embodiment is a device for capturing radiographic images of a breast of a subject. The mammography apparatus 12 is not limited to being employed with a subject in a standing state, and may be a device that images the breast of a subject when the subject is in a seated state seated in a chair (including a wheelchair), as long as it is a device capable of separately imaging the left and right breast of a subject that has at least the upper body in an upright state.

The mammography apparatus 12 is provided with a radiation source 24 that faces an imaging face 27 of an imaging table 26, and radiation R is irradiated from the radiation source 24 toward the imaging face 27.

During capture of a radiographic image of the breast of a subject, either the left or the right breast of the subject is pressed by an upper press member 28 and a lower press member 30, the breast is fixed by being pressed between the upper press member 28 and the lower press member 30, and radiation R is irradiated from the radiation source 24 onto the fixed breast. A radiation detector 22 detects the radiation R irradiated after passing through the breast. A radiographic image of the breast is generated based on the radiation R detected by the radiation detector 22.

Figure 2:
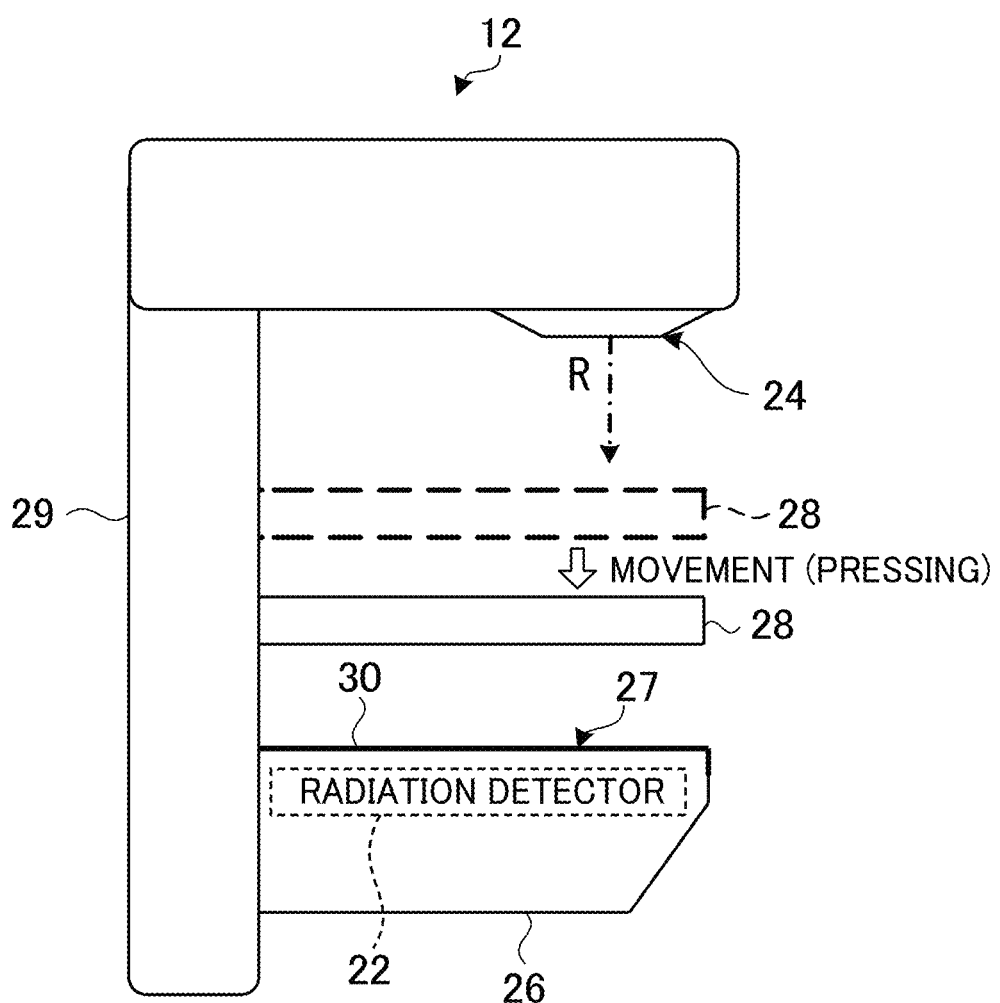
FIG. 2 is a side view to explain pressing of a breast using an upper press member of a first exemplary embodiment.

FIG. 2 is a side view for explaining pressing of a breast by the upper press member 28 in the present exemplary embodiment. The upper press member 28 is an example of a first press member of the present disclosure, which is a plate shaped press member (called a "press plate"), and the upper press member 28 presses downward from above the breast (from the head side of the subject). The upper press member 28 is accordingly held by a holder 29 so as to be capable of sliding movement between the imaging face 27 and the radiation source 24, with a variable separation to the imaging face 27.

As illustrated in FIG. 2, when the breast is being pressed by the upper press member 28, the upper press member 28 is moved in the direction approaching the imaging face 27.

A material through which the radiation R penetrates is employed in the upper press member 28. Polyethylene terephthalate is employed in the upper press member 28 of the present exemplary embodiment as a thermoplastic resin material. The material employed in the upper press member 28 is not limited thereto, and materials such as polycarbonate, acrylic, and polypropylene may be employed.

Figure 3:
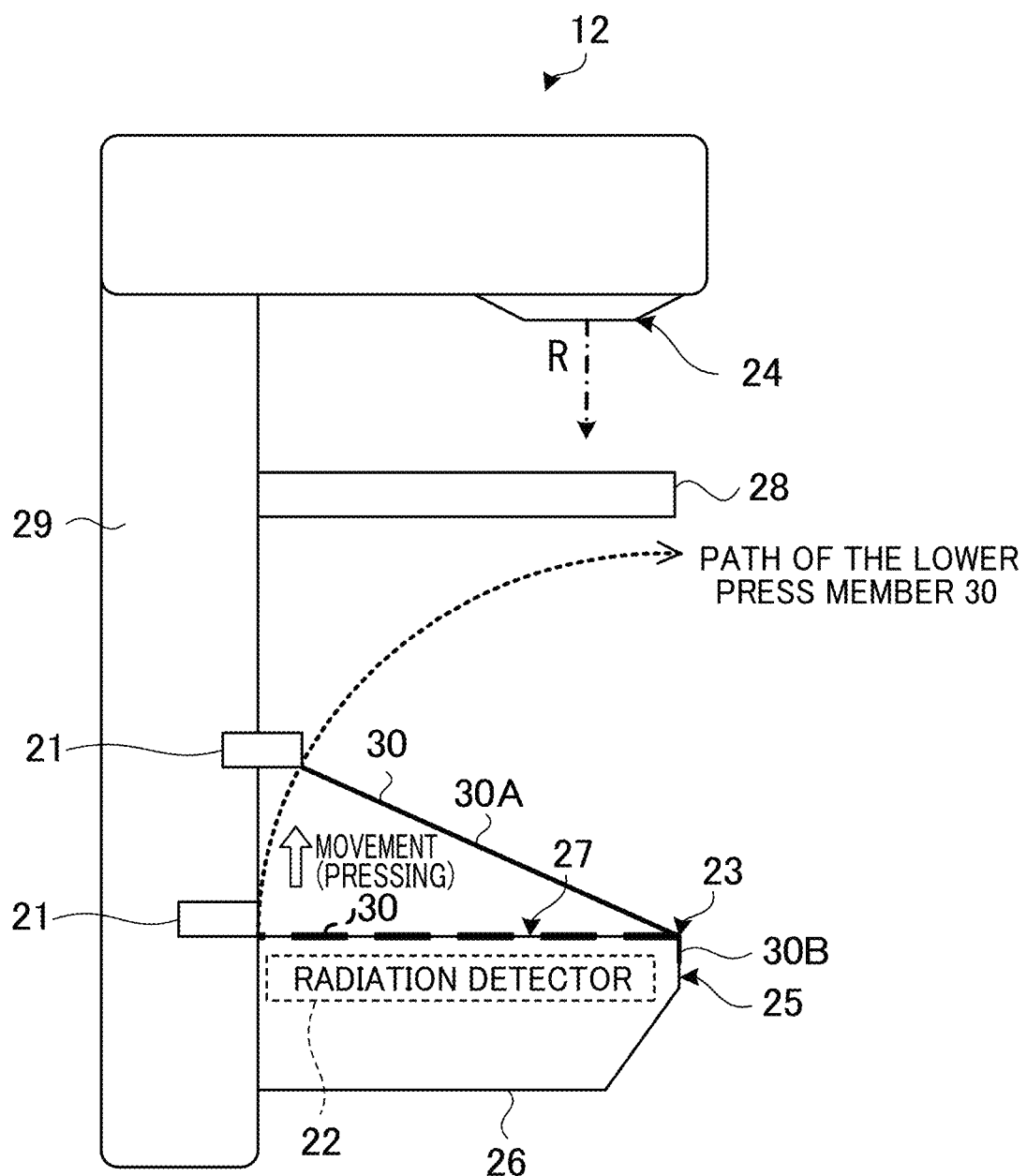
FIG. 3 is a side view to explain pressing of a breast using a lower press member of the first exemplary embodiment.
Figure 4:
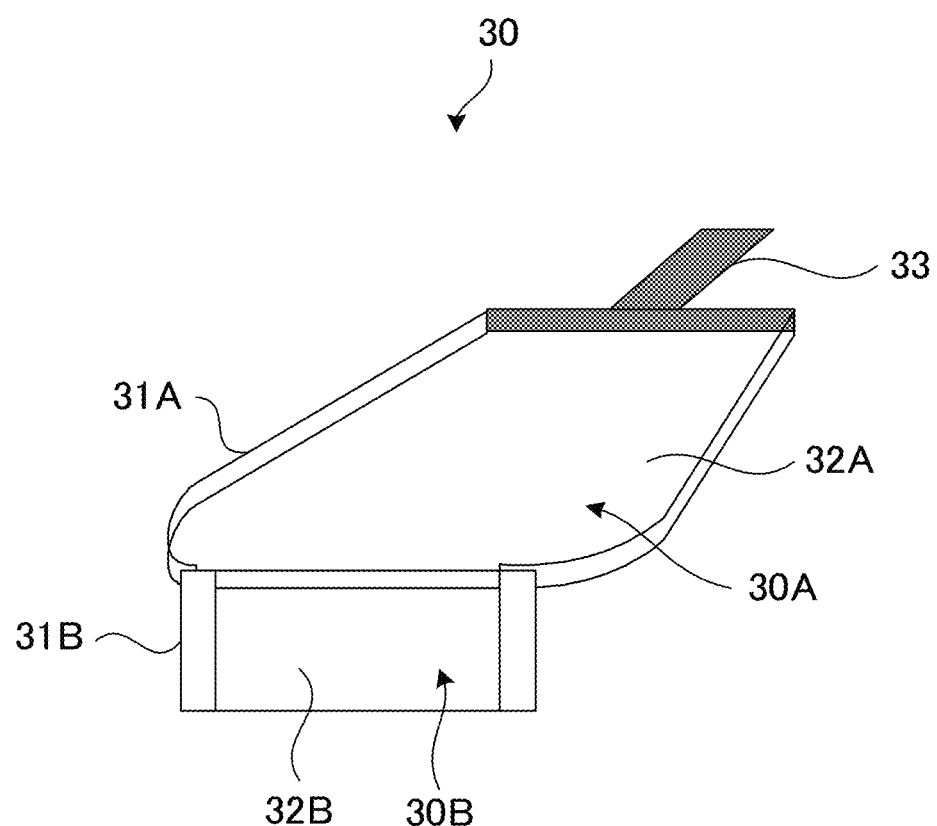
FIG. 4 is a perspective view illustrating an example of a configuration of a lower press member of the first exemplary embodiment.

FIG. 3 is a side view to explain pressing of a breast by the lower press member 30 of the present exemplary embodiment. FIG. 4 is a perspective view to explain an example of a configuration of the lower press member 30 of the present exemplary embodiment. The lower press member 30 is an example of a second press member of the present disclosure, and is equipped with a film shaped member that is the main configuration of the portion holding the breast and presses the breast upward from below (from the feet side of the subject). The far side end portion of the lower press member 30 at the opposite side to the chest wall side is accordingly held by the holder 29 so as to be capable of sliding movement between the imaging face 27 and the radiation source 24, with a variable separation between the far side end portion and the imaging face 27.

As illustrated in FIG. 4, the lower press member 30 of the present exemplary embodiment includes a press portion 30A, a fixed portion 30B, and a support portion 33.

The press portion 30A contacts the lower surface of the breast, and presses the breast. In the press portion 30A, a film 32A is stretched across inside of a frame 31A that is trapezoidal shaped in plan view, and the film 32A contacts the lower surface of the breast. The fixed portion 30B is fixed to a chest wall face 25 (see FIG. 3) of the imaging table 26, which contacts the chest wall of the subject. In the fixed portion 30B, a film 32B is stretched across inside of a frame 31B.

The support portion 33 is attached to the holder 29 by a lower press member holding portion 21 so as to be capable of sliding movement between the imaging face 27 and the radiation source 24. When the breast is pressed upward from below, the support portion 33 is moved in the direction away from the imaging face 27. In such cases, as illustrated in FIG. 3, due to the fixed portion 30B being fixed to the chest wall face 25, the lower press member 30 rotates about an axis of a corner portion 23, as illustrated in FIG. 3, and the film 32A bows. When the lower press member 30 is being moved in the direction away from the imaging face 27, due to the end portion of the support portion 33 moving from the holder 29 side toward the chest wall face 25 side, as illustrated in FIG. 3, the lower press member holding portion 21 extends from the holder 29 side toward the chest wall face 25 side according to movement of the support portion 33. A damper is an example of the lower press member holding portion 21. As is apparent from FIG. 3 and FIG. 4, the corner portion 23 is positioned at the end portion on the side of the chest wall, and the support portion 33 and the lower press member holding portion 21 are positioned at the far side end portion, that is at the opposite side to the chest wall side end portion.

Similar materials to those of the upper press member 28 are employed in the films 32A, 32B of the lower press member 30 in the present exemplary embodiment. However, although the upper press member 28 is plate shaped, the lower press member 30 differs in being film shaped. A frame of a metal such as aluminum or steel special use stainless (SUS) is employed as the frame 31A of the lower press member 30.

The components of the upper press member 28 and the lower press member 30 are not limited to those of the present exemplary embodiment. For example, the upper press member 28 may be a film shaped member similar to the film 32A of the press portion 30A illustrated in FIG. 4, and the lower press member 30 may be a plate shaped member. Note that, by employing a film shaped member, due to the film shaped member bowing according to the shape of the breast, an effect is obtained of reducing the pain of a subject more than when a plate shaped member is employed.

The lower press member 30 when a film shaped member is employed as the main configuration of the portion holding the breast is not limited to the structure illustrated in FIG. 4. For example, the frame 31A may be omitted, and a film shaped member corresponding to the film 32A may be stretched between the holder 29 and the chest wall face 25, and fixed to the lower press member holding portion 21 and the chest wall face 25.

The radiation detector 22 on which the radiation R that passes through the upper press member 28, the breast, the lower press member 30, and the imaging face 27 is irradiated, and for detecting this radiation R is housed inside the imaging table 26. A radiographic image is generated by making the radiation R detected by the radiation detector 22 visible. The radiation detector 22 is a detector that receives irradiation with the radiation R, records image data expressing the radiographic image, and outputs the recorded image data. Charges for each pixel generated according to the amount of irradiated radiation R are detected as image data.

There are no particular limitations to the type of the radiation detector 22 in the present exemplary embodiment. For example, an indirect conversion type of radiation detector may be employed in which the radiation R is converted into light, and the converted light is converted into charge, or a direct conversion type of radiation detector may be employed in which the radiation R is directly converted into charge.

In the present exemplary embodiment, the image data representing the radiographic image output from the radiation detector 22 of the mammography apparatus 12 is transmitted to the console 16. The console 16 in the present exemplary embodiment uses an imaging menu and various information acquired from an external system or the like through a wireless communication Local Area Network (LAN) to control the mammography apparatus 12.

Figure 5:
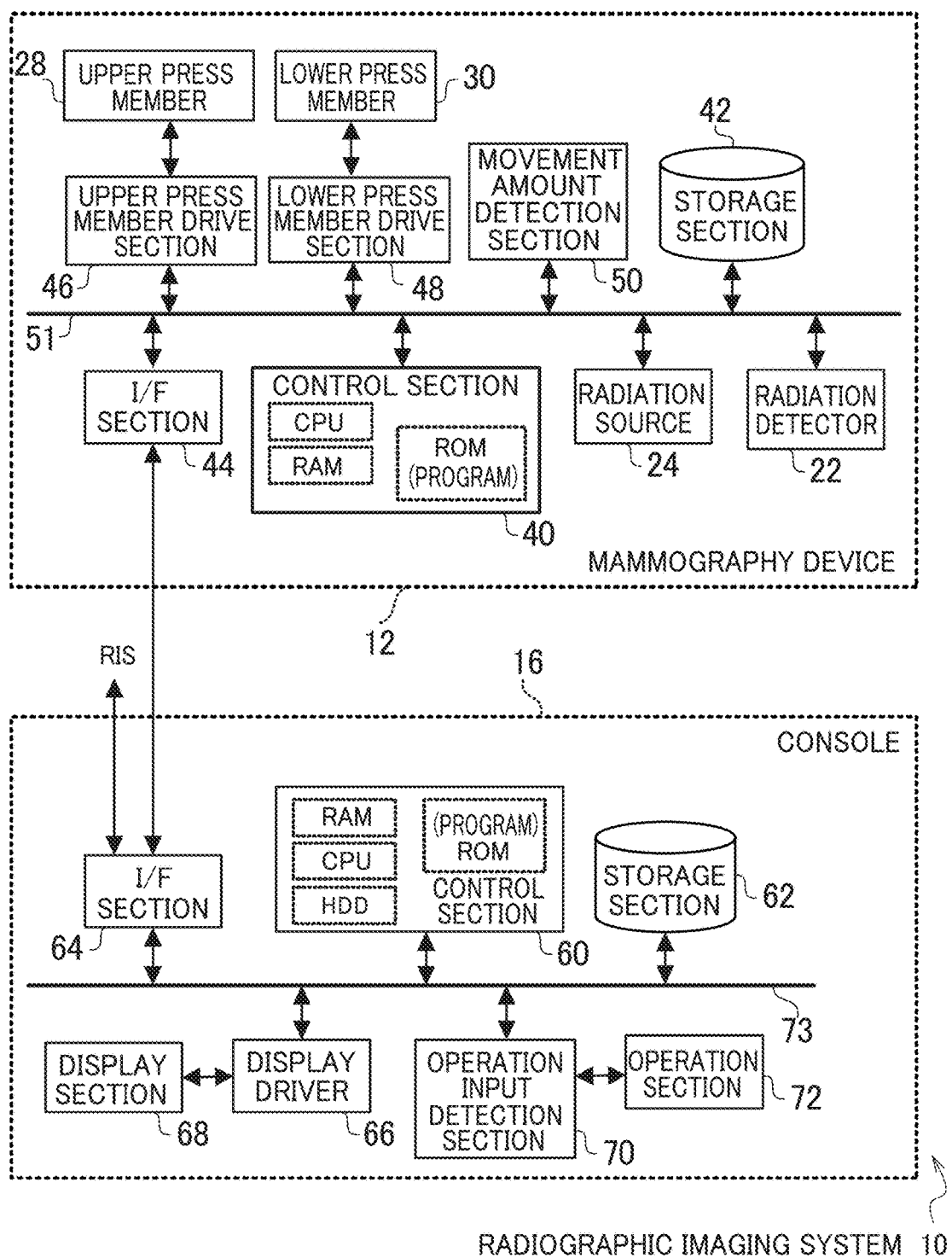
FIG. 5 is a block diagram illustrating an electrical configuration of a mammography apparatus (device) and console according to the first exemplary embodiment.

FIG. 5 is a block diagram illustrating a configuration of an electrical system of the mammography apparatus 12 and the console 16 of the present exemplary embodiment.

The console 16 is an example of a control device, and is a server computer. As illustrated in FIG. 5, the console 16 includes a control section 60, a storage section 62, a display driver 66, a display section 68, an operation input detection section 70, an operation section 72, and an interface (I/F) section 64. The control section 60, the storage section 62, the display driver 66, the operation input detection section 70, and the I/F section 64 are mutually connected together through a bus 73, such as a system bus or a control bus, so as to be capable of exchanging various information between each other.

The control section 60 of the present exemplary embodiment controls the overall operation of the console 16. The control section 60 includes a central processing unit (CPU), read only memory (ROM), random access memory (RAM), and a hard disk drive (HDD). Various processing programs for executing on the CPU are pre-stored on the ROM. The RAM temporarily stores various data. The HDD stores and holds various data. The HDD may be a solid state drive (SSD), and may also be employed in combination as the storage section 62.

The display section 68 displays various information. The display driver 66 controls the display of various information on the display section 68.

The operation section 72 is used by a user for input, such as for input of instructions and various information related to capturing radiographic images or the like. The operation section 72 is not particularly limited, and examples thereof include various switches, a touch panel, a stylus, multiple keys, and a mouse. When the operation section 72 is implemented by a touch panel, the operation section 72 may be integrated with the display section 68. The operation input detection section 70 detects the operational state of the operation section 72.

The I/F section 64 performs transmission of various information between with the mammography apparatus 12 and an external system (such as an RIS) via wireless communication or wired communication.

Image data and the like of radiographic images captured by the mammography apparatus 12 are stored in the storage section 62. Specific examples of the storage section 62 include an HDD and an SDD.

The mammography apparatus 12 in the present exemplary embodiment includes the radiation detector 22, the radiation source 24, the upper press member 28, the lower press member 30, a control section 40, a storage section 42, an I/F section 44, an upper press member drive section 46, a lower press member drive section 48, and a movement amount detection section 50.

The radiation detector 22, the radiation source 24, the control section 40, the storage section 42, the I/F section 44, the upper press member drive section 46, the lower press member drive section 48, and the movement amount detection section 50 are mutually connected together through a bus 52 such as a system bus or a control bus so as to be capable of exchanging various information with each other.

The control section 40 is an example of a control section of the present disclosure, and controls the overall operation of the mammography apparatus 12. The control section 40 of the present exemplary embodiment controls, during the capture of radiographic images, the radiation detector 22, the radiation source 24, the upper press member drive section 46, the lower press member drive section 48, and the movement amount detection section 50. The control section 40 of the present exemplary embodiment includes a CPU, ROM, and RAM. Various processing programs for executing on the CPU are pre-stored on the ROM. The RAM temporarily stores various data.

Figure 6:
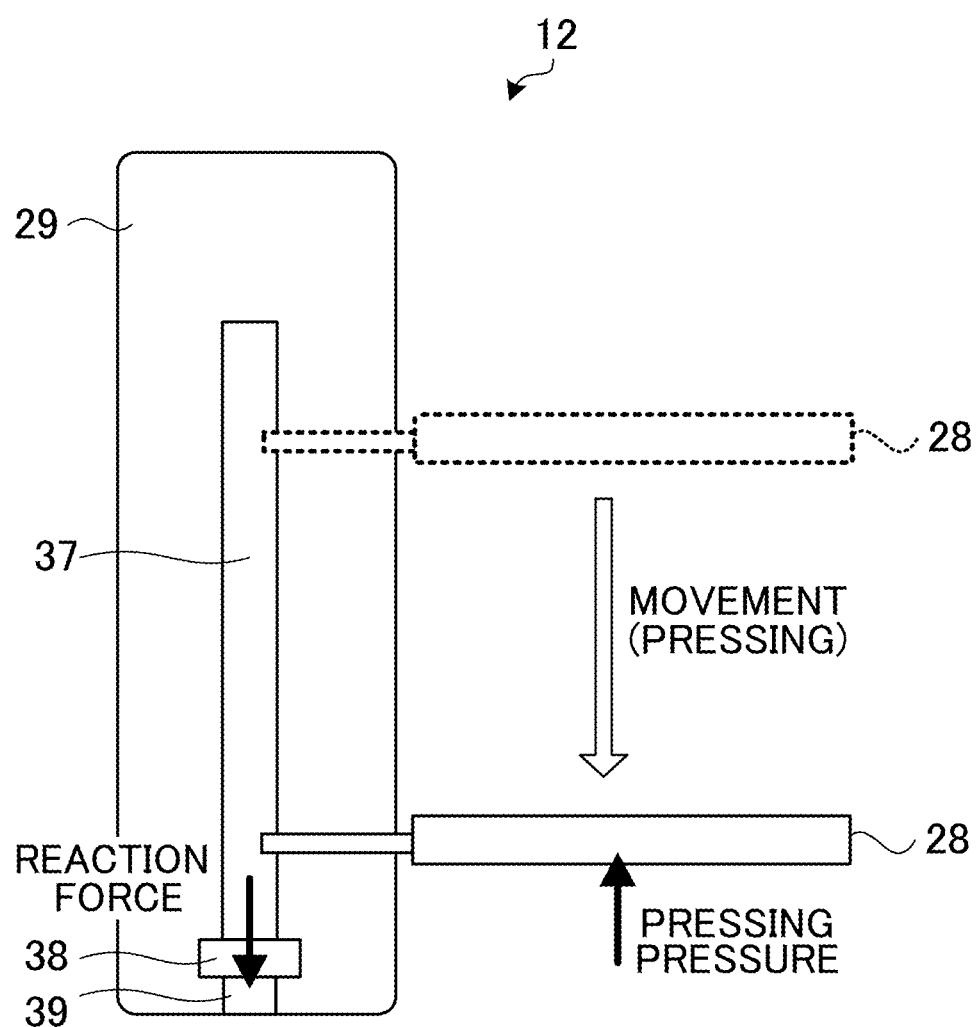
FIG. 6 is an explanatory diagram to explain an example of pressing pressure detection when pressing pressure is detected from the load on a motor in the first exemplary embodiment.

The upper press member drive section 46 drives (slides) the upper press member 28 between the imaging face 27 and the radiation source 24. The lower press member drive section 48 drives (slides) the support portion 33 of the lower press member 30 between the imaging face 27 and the radiation source 24. The upper press member drive section 46 and the lower press member drive section 48 in the present exemplary embodiment include a motor 38 (see FIG. 6) as a drive source, and pressing pressure is detected based on the load acting on the motor 38, and the detection result is output. FIG. 6 is an explanatory diagram to explain an example of detecting the pressing pressure in such cases. In FIG. 6, explanation is given of a case in which the pressing pressure is detected based on the load acting on the motor 38 as the drive source of the upper press member 28, however, similar applies to cases employing the lower press member 30. A strain gauge 39 such as a load cell, a ball screw 37, and the motor 38 is provided inside the holder 29. The upper press member 28 is supported by the ball screw 37, and moves by sliding between the imaging face 27 and the radiation source 24 by driving the motor 38. The strain gauge 39 detects the pressing pressure of the upper press member 28 by detecting the reaction force to the pressing pressure of the upper press member 28.

The method for detecting the pressing pressure is no limited to this, and, for example, a pressure sensor or the like may be provided for detecting the pressing pressure on the upper press member 28 and the lower press member 30.

The movement amount detection section 50 of the present exemplary embodiment is provided inside the holder 29 and detects movement amount of the upper press member 28 and the lower press member 30. A potentiometer may be, for example, employed as the movement amount detection section 50. The movement amount detection section 50 detects the relative movement amount between the upper press member 28, and the support portion 33 of the lower press member 30, namely, detects the movement amount corresponding to the distance between the upper press member 28 at the position of the holder 29, and the support portion 33 of the lower press member 30. In the present exemplary embodiment, as a method by which the movement amount detection section 50 detects the movement amount, the movement amount is detected based on initial positions of the upper press member 28 and the support portion 33 of the lower press member 30, and on positions after moving (slide positions) of the upper press member 28 and the support portion 33 of the lower press member 30. However, there is no limitation thereto.

The I/F section 44 performs communication of various information with the console 16 using wireless communication or wired communication.

Various information and the like is stored in the storage section 42. Specific examples of the storage section 42 include an HDD and an SDD.

In the present exemplary embodiment, various programs stored in the control section 40 of the mammography apparatus 12 and the control section 60 of the console 16 are stored in advance on ROMs of the control section 40 and the control section 60, however there is no limitation thereto, and the programs may be stored on a recording medium such as a compact disk read only memory (CD-ROM) or a removable disk, and then installed on the ROM or the like from the recording medium. The programs may also be installed on the ROM or the like from an external device over a communications line, such as the internet.

Next, explanation follows regarding operation of the mammography apparatus 12 of the present exemplary embodiment, with reference to the drawings.

In the radiographic imaging system 10 of the present exemplary embodiment, in order to start imaging the breast of the subject, the user first positions the breast of the subject on the imaging face 27 of the imaging table 26 of the mammography apparatus 12. Then, after the breast of the subject has been positioned on the mammography apparatus 12, the user instructs the start of imaging using the operation section 72 of the console 16. The instruction input to the operation section 72 to start imaging is detected by the operation input detection section 70, and is transmitted to the mammography apparatus 12 through the I/F section 64.

Figure 7:
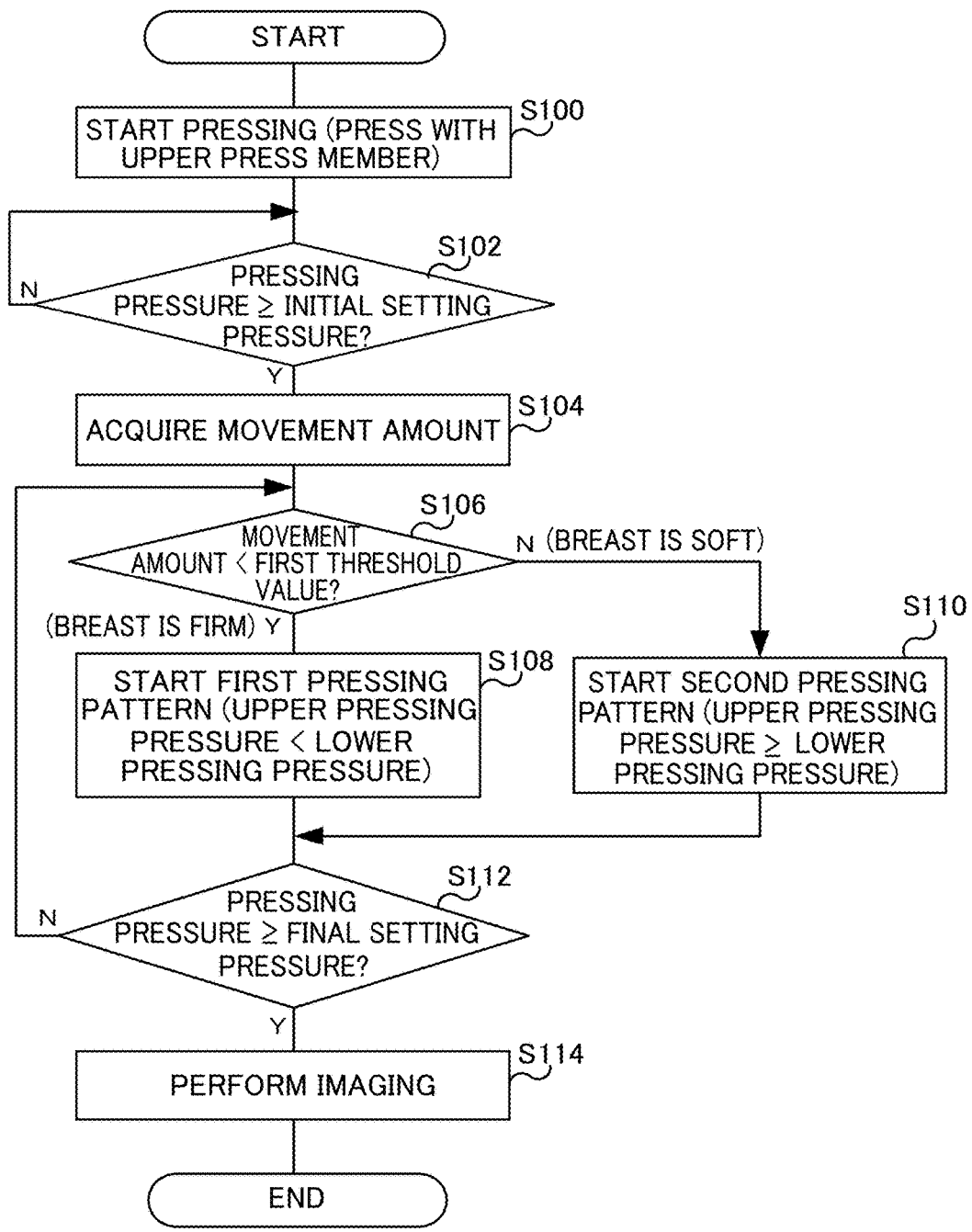
FIG. 7 is a flowchart illustrating a flow of imaging processing executed by a control section of a mammography apparatus of the first exemplary embodiment.

When the instruction to start imaging the radiographic image has been received from the console 16 through the I/F section 44, imaging processing is executed in the mammography apparatus 12 of the present exemplary embodiment. FIG. 7 illustrates a flowchart representing an example of a flow of imaging processing executed by the control section 40 of the mammography apparatus 12. In the mammography apparatus 12 of the present exemplary embodiment, image processing is executed is implemented by the control section 40 executing a program stored in its own ROM.

At step S100, the control section 40 starts pressing the breast. In the mammography apparatus 12 of the present exemplary embodiment, the lower press member 30 is not moved at the start of pressing, and only the upper press member 28 is moved, and the breast is pressed downward by the upper press member 28 from above. The control section 40 gradually increases the magnitude of the pressing pressure by moving the upper press member 28 using the upper press member drive section 46 so as to press the breast.

At the next step S102, the control section 40 determines whether or not the pressing pressure with which the upper press member 28 presses the breast is equal to or greater than an initial setting pressure. In the mammography apparatus 12 of the present exemplary embodiment, a first pressing pressure of the upper press member 28 and a second pressing pressure of the lower press member 30 are set using the pressing pressure when the breast is pressed with the initial setting pressure, and the movement amount detected by the movement amount detection section 50. In the present exemplary embodiment, from the perspective of avoiding setting error due to noise, a pressing pressure when the upper press member 28 presses the breast with a force of 30N is employed as the initial setting pressure, however there is no particular limitation thereto. Generally, the mammography apparatus 12 press the breast so that the pressing pressure reaches a pre-set value (a final set pressure, described in detail later) that is set in advance based on an appropriate firmness for capturing radiographic images. Therefore, the initial setting pressure may be determined according to this pre-set value.

Negative determination is made at step S102 when the pressing pressure is less than the initial setting pressure, and a standby state is adopted while pressing of the breast is continued. However, affirmative determination is made when the pressing pressure is equal to or greater than the initial setting pressure, and processing transitions to step S104.

At step S104, the control section 40 acquires the movement amount from the movement amount detection section 50. In such cases, since the control section 40 only moves the upper press member 28 and does not move the lower press member 30, the movement amount of the upper press member 28 (the amount of approach toward the imaging face 27) is acquired as the movement amount.

Next, at step S106, the control section 40 determines whether or not the acquired movement amount is less than a first threshold value. The first threshold value is a threshold value corresponds to a predetermined firmness of the breast, as described below.

Figure 8:
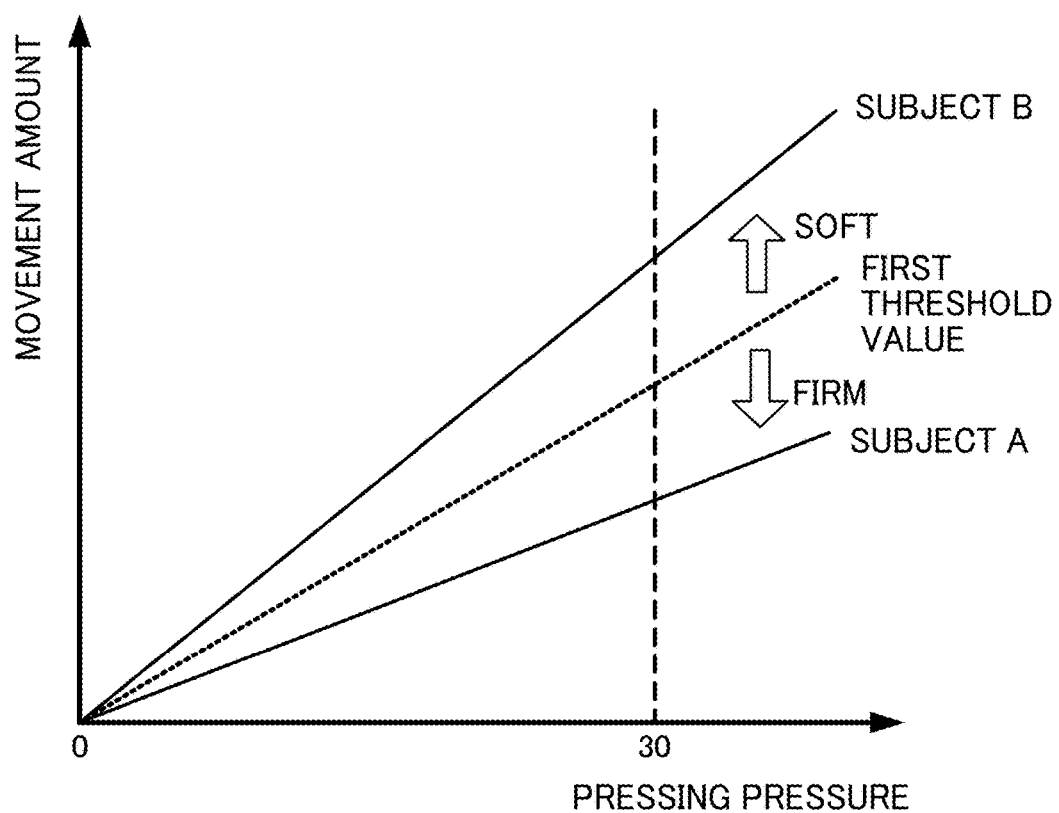
FIG. 8 is a graph illustrating an example of a correspondence relationship between pressing pressure on a breast and movement amount of an upper press member and a lower press member.

As described above, in the mammography apparatus 12 of the present exemplary embodiment, the first pressing pressure of the upper press member 28 and the second pressing pressure of the lower press member 30 are set using the pressing pressure on the breast, and the movement amount detected by the movement amount detection section 50. FIG. 8 is a graph illustrating an example of a correspondence relationship between the pressing pressure and the movement amount.

As illustrated in FIG. 8, when a breast is being pressed by at least one of the upper press member 28 or the lower press member 30, the movement amount of at least one of the upper press member 28 or the lower press member 30 changes according to the pressing pressure. The firmer the breast, the smaller the amount of change in the breast accompanying the rise in pressing pressure, and the harder the breast is to squash. Thus, the movement amount is smaller the firmer the breast.

The control section 40 of the present exemplary embodiment acquires in advance the first threshold value from the correspondence relationship between the pressing pressure on a breast of a predetermined firmness (for example, a standard firmness) and the movement amount, and sets a pressing pressure (a first pressing pattern, described in detail later) for cases in which the breast is firm when the movement amount according to the pressing pressure is less than the first threshold value.

Affirmative determination is made at step S106 when the movement amount is less than the first threshold value (movement amount<first threshold value) and processing transitions to step S108. When affirmative determination is made at step S106, these are cases in which the breast of the subject is firmer than the predetermined firmness, as described above. In a case illustrated in FIG. 8, since the movement amount in response to the initial setting pressure (30N) is less than the first threshold value, for the breast of the subject A, a pressing pressure for cases in which the breast is firmer than the predetermined firmness (the first pressing pattern, described in detail later) is set.

The inventor of the present disclosure have found that there is a tendency for pain of a subject to be reduced more when pressed from below than when pressed from above in cases of firm breasts. Thus, in cases in which the breast is firmer than the predetermined firmness, the control section 40 controls the upper press member drive section 46 and the lower press member drive section 48 such that the breast is pressed with a pressing pattern (referred to below as the first pressing pattern) in which the second pressing pressure with the lower press member 30 is larger than the first pressing pressure with the upper press member 28.

Thus, at step S108, the control section 40 starts pressing with the first pressing pattern, and then processing transitions to step S112.

However, negative determination is made at step S106 when the acquired movement amount is equal to or greater than the first threshold value (movement amount≥first threshold value). When negative determination is made at step S106, these are cases in which the breast of the subject is softer than the predetermined firmness. In a case illustrated in FIG. 8, since the movement amount in response to the initial setting pressure is equal to or greater than the first threshold value, the breast of the patient B is determined to be softer than the predetermined firmness.

In the mammography apparatus 12 of the present exemplary embodiment, when the breast is softer than the predetermined firmness, the control section 40 controls the upper press member drive section 46 and the lower press member drive section 48 so as to press the breast with a pressing pattern in which the upper pressing pressure (the first pressing pressure) is equal to or greater than the lower pressing pressure (the second pressing pressure) (this mode is referred to below as the "second pressing pattern").

Thus, at step S110, the control section 40 starts pressing with the second pressing pattern, and then processing transitions to step S112.

The breast of the subject is pressed by the upper press member 28 and the lower press member 30 by the processing of step S108 or S110.

At step S112, the control section 40 determines whether or not the pressing pressure by the upper press member 28 and the lower press member 30 (the first pressing pressure with the upper press member 28+the second pressing pressure with the lower press member 30) is equal to or greater than the final setting pressure that is larger than the initial setting pressure. Negative determination is made when the pressing pressure is less than the final setting pressure, and processing returns to step S106, and the processing of steps S106 to S110 is repeated while continuing pressing of the breast by moving the upper press member 28 and/or the lower press member 30.

However, affirmative determination is made at step S112 when the pressing pressure with the upper press member 28 and the lower press member 30 is equal to or greater than the final setting pressure, and processing transitions to step S114. When affirmative determination is made at step S112, movement of the upper press member 28 and the lower press member 30 is stopped in the mammography apparatus 12 of the present exemplary embodiment.

At step S114, the control section 40 controls the radiation detector 22 and the radiation source 24, and, after capturing a radiographic image of the breast of the subject, ends the present imaging processing. Specifically, the control section 40 causes the radiation source 24 to irradiate the breast of the subject with radiation R according to the imaging menu, or the like. Under control of the control section 40, the radiation detector 22 detects the radiation R that has passed through the breast, and outputs, to the console 16, image data of a radiographic image according to the detected radiation R.

Note that, as a variation of the present exemplary embodiment, at steps S108 and S110, the upper pressing pressure (first pressing pressure) may be equal to or lower than the lower pressing pressure (second pressing pressure) in the first pressing pattern, and the upper pressing pressure (first pressing pressure) may be larger than the lower pressing pressure (second pressing pressure) in the second pressing pattern.

Second Exemplary Embodiment

Explanation has been given in the first exemplary embodiment of a case in which the pressing pressure is set using the pressing pressure on a breast and the movement amount (the relative movement amount between the upper press member 28 and the support portion 33 of the lower press member 30). Explanation follows in the present exemplary embodiment of a case in which the pressing pressure is set using the movement amount and a contact surface area of a breast with the lower press member 30.

A breast is deformed and extended by pressing with at least one of the upper press member 28 or the lower press member 30, while changing the contact surface area of contact with at least one of the upper press member 28 or the lower press member 30. The way in which the breast is extended differs between cases in which the breast is firm and cases in which the breast is soft. The firmer the breast, the more difficult to extend the breast, and the more difficult it is to increase the contact surface area.

Thus, in the control section 40 of the present exemplary embodiment, the first pressing pressure of the upper press member 28 and the second pressing pressure of the lower press member 30 are set using the movement amount, and the contact surface area with which a breast contacts the lower press member 30.

Figure 9:
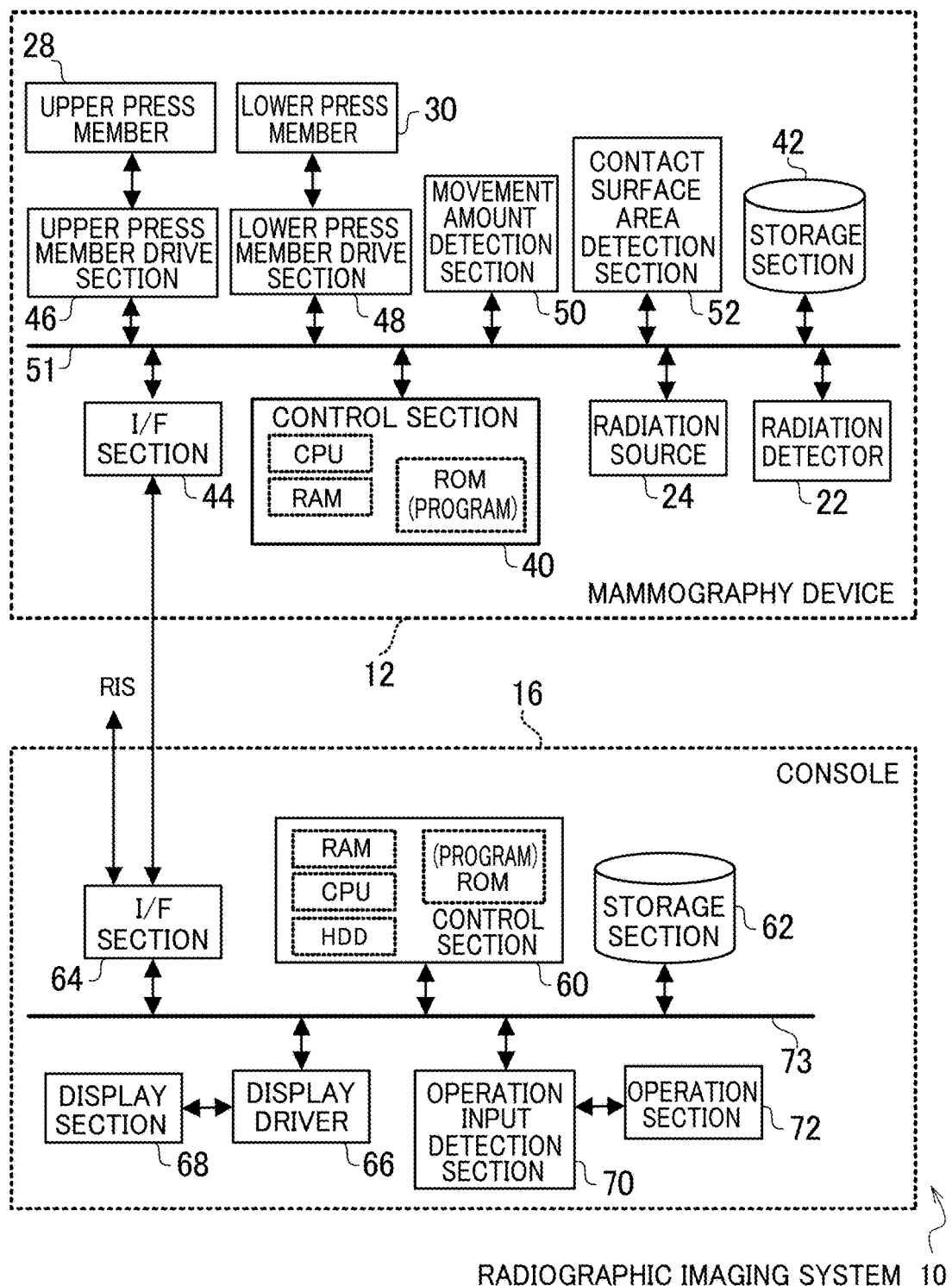
FIG. 9 is a block diagram illustrating an electrical configuration of a mammography apparatus and console according to a second exemplary embodiment.

FIG. 9 is a block diagram illustrating a configuration of an electrical system of the mammography apparatus 12 and the console 16 of the present exemplary embodiment.

As illustrated in FIG. 9, the mammography apparatus 12 of the present exemplary embodiment differs from the mammography apparatus 12 of the first exemplary embodiment (see FIG. 5) in the point that a contact surface area detection section 52 is provided.

Figure 10:
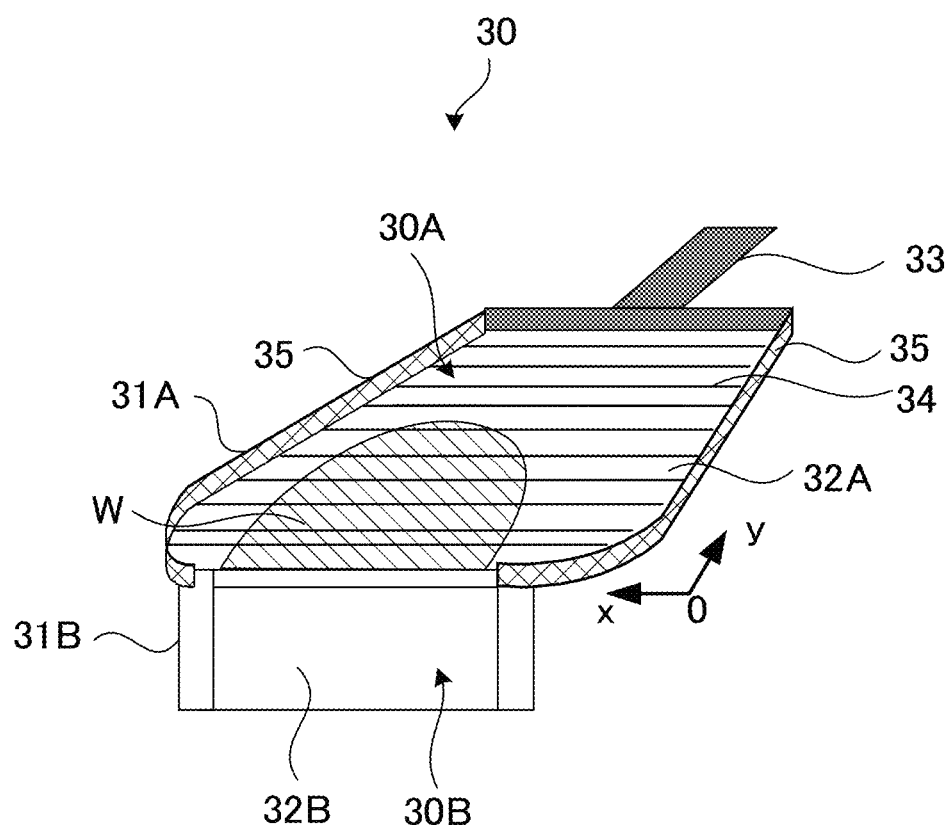
FIG. 10 is a perspective view illustrating an example of a configuration of a lower press member according to the second exemplary embodiment.

As a sensor for detecting the contact surface area, the contact surface area detection section 52 of the present exemplary embodiment includes wires 34 and a pair of electrodes 35 that are provided at the lower press member 30 (see FIG. 10). FIG. 10 is a perspective view illustrating an example of a configuration of the lower press member 30 in the present exemplary embodiment. For explanation, the contact portion of the breast is indicated by contact portion W in FIG. 10. Further, in FIG. 10, the direction from the chest wall face 25 toward the support portion 33 is indicated as the y direction, and the x direction is a direction orthogonal to the y direction.

On the film 32A of the press portion 30A of the lower press member 30, plural wires 34 extending parallel to the chest wall face 25 of the imaging table 26 are provided at predetermined intervals from the chest wall side toward the support portion 33. The wires 34 are preferably metal wires having a diameter of 1 μm or less, in order to prevent effects imparted to the radiographic images being captured.

The pair of electrodes 35 connected to end portions of the plural wires 34 are provided at the frame 31A of the press portion 30A of the lower press member 30.

The electrodes 35 are connected through connection wires (not illustrated in the drawings) to a current detection circuit (not illustrated in the drawings) provided inside the imaging table 26. The current detection circuit applies a voltage to the electrodes 35, detects current flowing in each of the wires 34, and detects changes in the respective resistance values of each of the wires 34. The current flowing in the wires 34 is preferably as small as possible from the perspectives of safety standards and giving electric shocks to the subject with current leakage. Further, it is preferable that no current is flowing through the wires 34 at least while radiographic images are being captured, and the current only flows in the wires 34 while the contact surface area is being detected.

Figure 11:
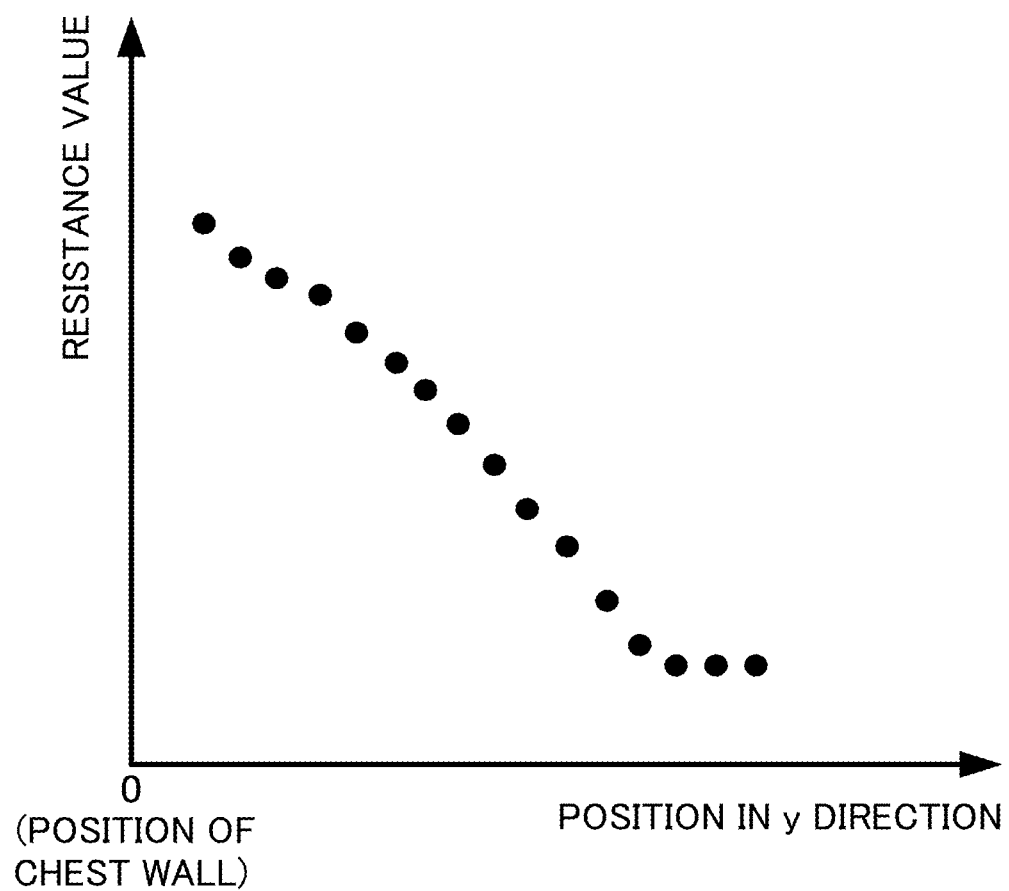
FIG. 11 is a graph illustrating a correspondence relationship between positions of each wire in a y direction and resistance values when a breast is in contact with the lower press member as illustrated in FIG. 10.
Figure 12:
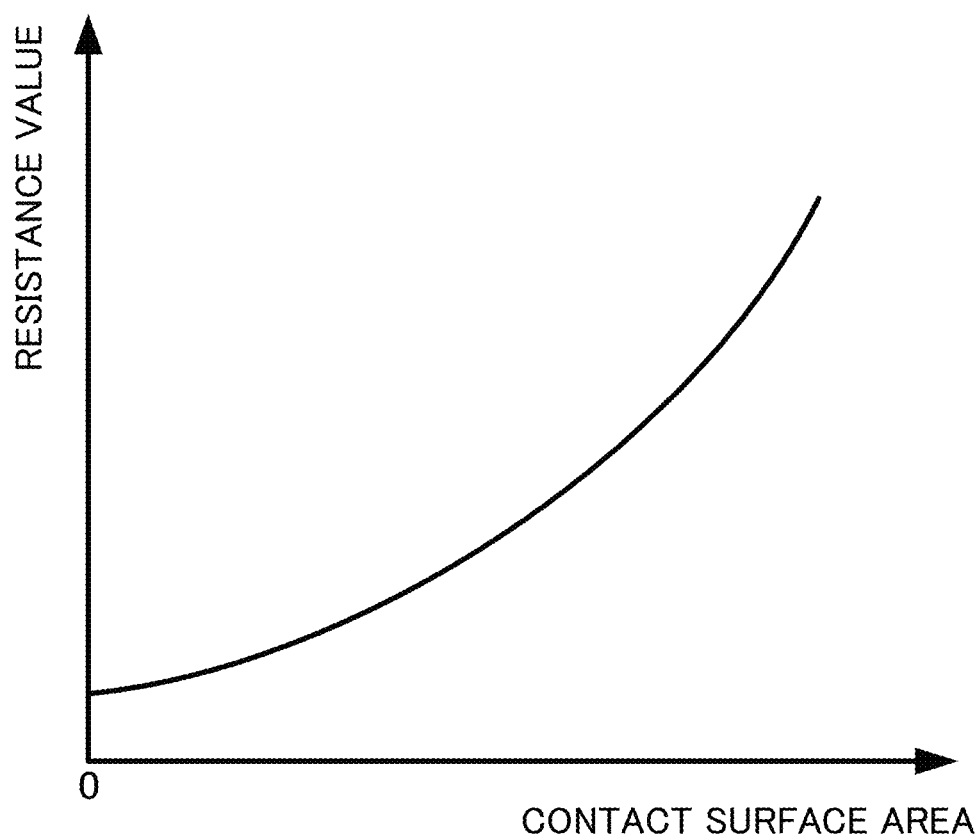
FIG. 12 is a graph illustrating a correspondence relationship between wire resistance value and contact surface area.

FIG. 11 is a graph illustrating a correspondence relationship between the position of each of the wires 34 in the y direction and resistance values in a case in which the breast contacts the lower press member 30 as illustrated in FIG. 10. FIG. 12 is a graph illustrating a correspondence relationship between resistance values of the wires 34 and contact surface area.

As illustrated in FIG. 12, the resistance values increase as the contact surface area gets larger. Thus, in cases in which the breast contacts the lower press member 30 over the contact portion W, as illustrated in FIG. 10, the resistance values of the wires 34 are larger at positions on the chest wall side, and the resistance values gradually decrease as the contact surface area (the contact portion W) decreases toward the holder 29, as illustrated in FIG. 11.

The contact surface area detection section 52 acquires the contact surface area corresponding to the resistance values of each of the wires 34 from the correspondence relationship illustrated in FIG. 12, and detects the contact surface area of the contact portion W by summing the contact surface area corresponding to all of the wires 34.

EXCLEAR®, manufactured by Fujifilm Corporation, may be used as the wires 34 and the electrodes 35 for detecting the contact surface area in this manner, however there is no limitation thereto. For example, any configuration may be applied having resistance values that change with contact of the breast, and that does not affect the radiographic images (or that has an effect that can be eliminated, or only has a small effect). The method for detecting the contact surface area is not limited to that of the present exemplary embodiment, and, for example, the contact surface area may be detected by installing a camera at a position facing the imaging face 27 and performing image analysis on images of the breast captured in a pressed state.

In the present exemplary embodiment, the contact surface area of the breast contacting only the lower press member 30 is detected, however there is no limitation thereto, and the contact of the breast contacting only the upper press member 28 may be detected. Moreover, the contact surface area of the breast contacting both the lower press member 30 and the contact surface area of the breast contacting the upper press member 28 may be detected, and the average value thereof may be employed.

Figure 13:
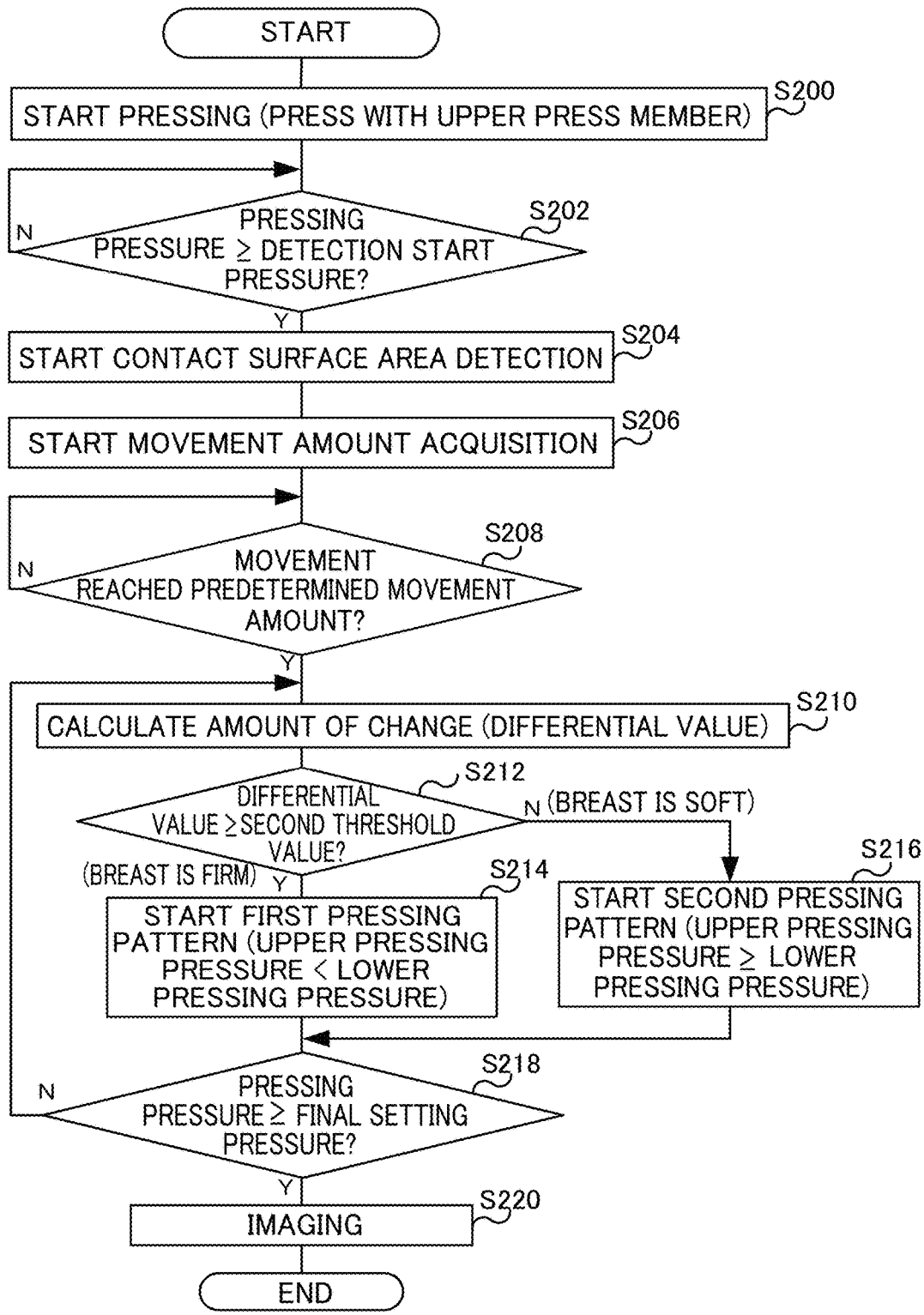
FIG. 13 is a flowchart illustrating a flow of imaging processing executed by a control section of a mammography apparatus of the second exemplary embodiment.

Next, explanation follows regarding imaging processing executed by the mammography apparatus 12 of the present exemplary embodiment. FIG. 13 is a flow chart illustrating an example of a flow of image processing executed by the control section 40 of the mammography apparatus 12 of the present exemplary embodiment.

Step S200 corresponds to step S100 of the image processing of the first exemplary embodiment (see FIG. 7). At step S200, the control section 40 starts pressing the breast with the upper press member 28.

Next, at step S202, the control section 40 determines whether or not pressing pressure with which the upper press member 28 is pressing the breast is equal to or greater than a detection start pressure. The contact surface area may not be appropriately detected when there is a gap between the breast and the upper press member 28, and/or a gap between the breast and the lower press member 30, and the portion of the breast in contact with the upper press member 28 and with the lower press member 30 is small. Thus, in the mammography apparatus 12 of the present exemplary embodiment, the amount of pressing pressure with which there are no gaps is predetermined as the detection start pressure, and detection of the contact surface area is started when the pressing pressure on the breast is equal to or greater than the detection start pressure.

Negative determination is made at step S202 when the pressing pressure is less than the detection start pressure, and a standby state is adopted while pressing by the upper press member 28 is continued. However, affirmative determination is made when the pressing pressure is equal to or greater than the detection start pressure, and processing transitions to step S204.

At step S204, the control section 40 starts to detect the contact surface area using the contact surface area detection section 52. At next step S206, the control section 40 starts detection of the movement amount using the movement amount detection section 50. The control section 40 associates the detected contact surface areas with the movement amounts, and then stores the detection results in the storage section 42.

Next at step S208, the control section 40 determines whether or not the movement amount indicates that the upper press member 28 has moved by the predetermined movement amount.

In the mammography apparatus 12 of the present exemplary embodiment, the first pressing pressure of the upper press member 28 and the second pressing pressure of the lower press member 30 are set using the movement amount and the contact surface area over the period in which the upper press member 28 is moved up to the predetermined movement amount.

Figure 14:
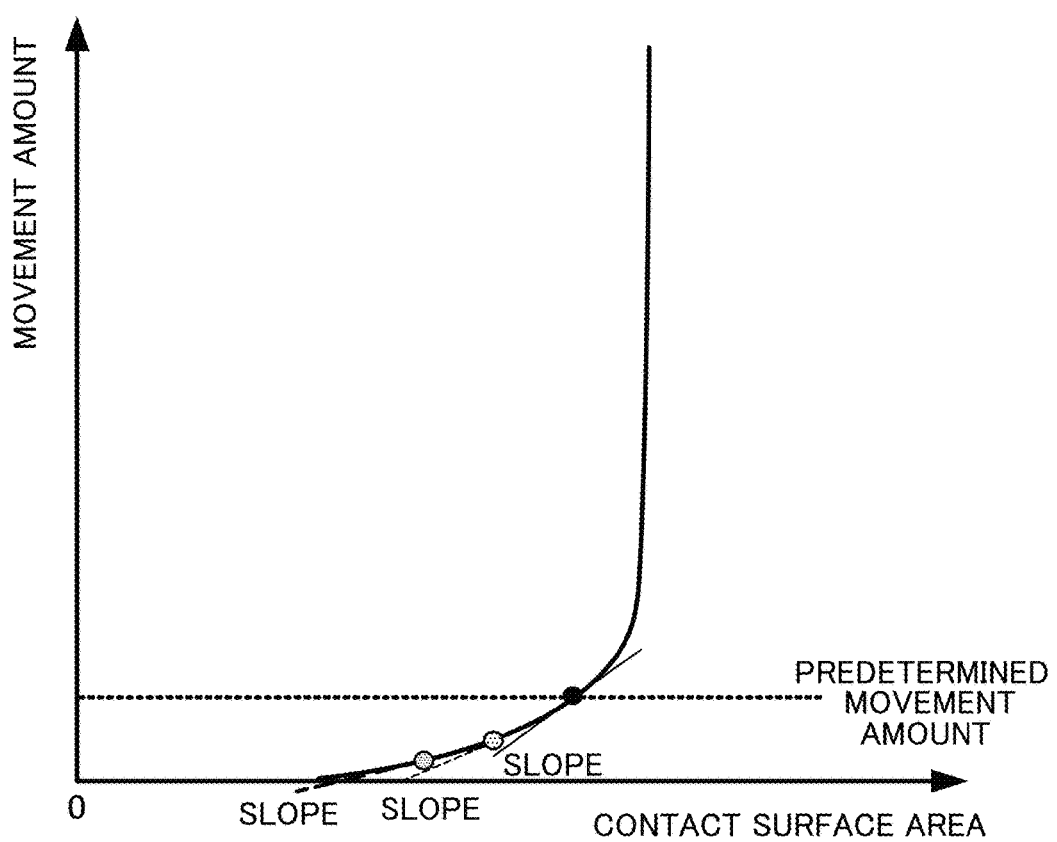
FIG. 14 is a graph illustrating an example of a correspondence relationship between the contact surface area of a breast and the movement amount of an upper press member and a lower press member.
Figure 15:
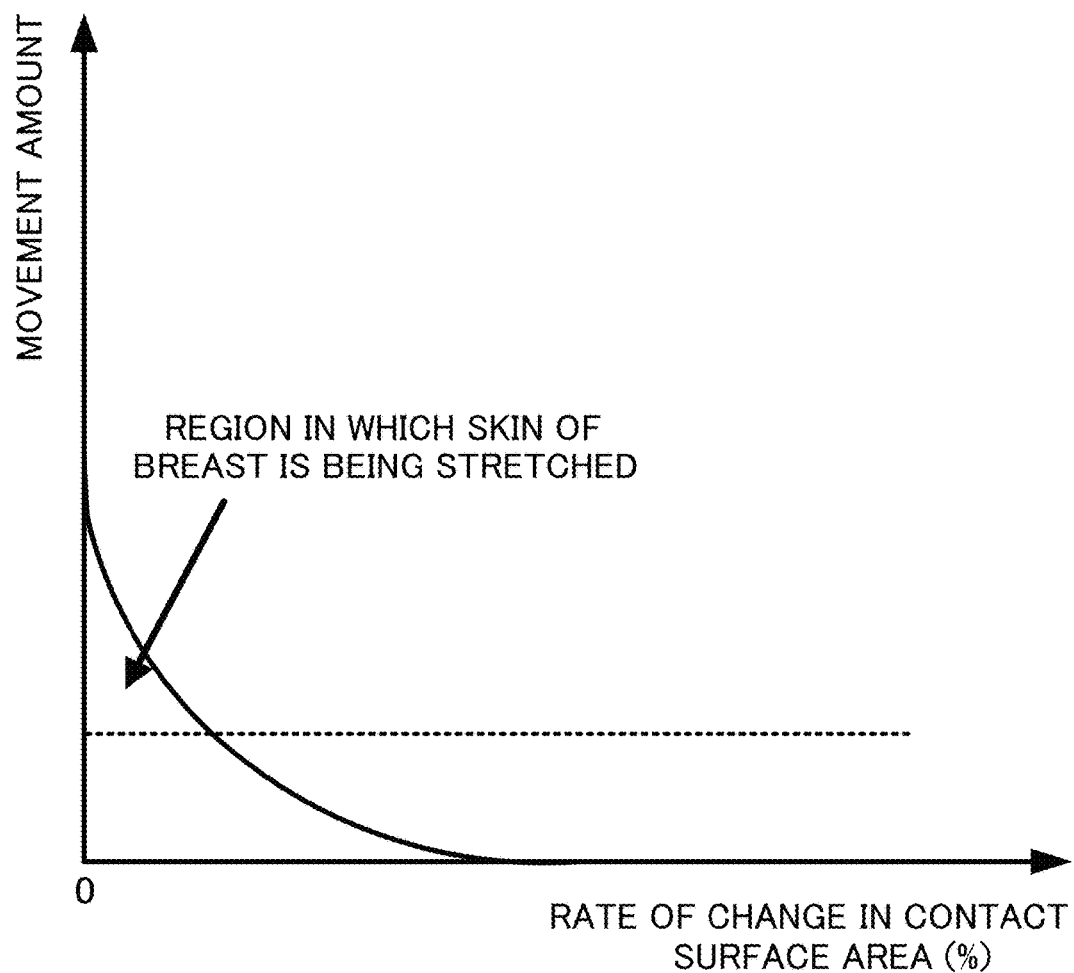
FIG. 15 is a graph illustrating an example of a correspondence relationship between rate of change in breast contact surface area and movement amount of an upper press member and a lower press member.

FIG. 14 is a graph illustrating an example of a correspondence relationship between the contact surface area and the movement amount as described above. FIG. 15 is a graph illustrating an example of a correspondence relationship between rate of change in the contact surface area and the movement amount as described above. The rate of change in contact surface area in FIG. 15 is derived by (currently detected value of contact surface area−immediately previously detected value of contact surface area)/the immediately previously detected contact surface area×100(%).

As illustrated in FIG. 14, as the breast is being pressed by at least one of the upper press member 28 or the lower press member 30, the contact surface area increases as the movement amount gets larger up to a certain extent, but then the change in the contact surface area substantially stops even though the movement amount is large. Moreover, as illustrated in FIG. 15, the rate of change in contact surface area becomes smaller the larger the movement amount, and the rate of change in the contact surface area substantially stops changing even though the movement amount is larger. This is a state in which pressure is increasing due to the skin of the breast being stretched and the movement amount is increasing, and is not a state in which the breast is pressed out overall. There is a concern that unnecessary pain might be caused if the breast of a subject is pressed more than necessary in a region in which the contact surface area, or the change in the rate of change in contact surface area, is not small.

In the present exemplary embodiment, the correspondence relationship as illustrated in FIG. 14 between the contact surface area and the movement amount over the period from the start of contact surface area detection up to the movement amount of at least one of the upper press member 28 and the lower press member 30 reaches the predetermined movement amount is obtained in advance. By using an amount of change in contact surface area, specifically the differential values of the graph illustrated in FIG. 14, determination is made as to whether or not extension of the breast is difficult, and whether or not it is difficult to make the contact surface area larger. The differential values of the graph illustrated in FIG. 14 are illustrated as the slopes of the graph at each detection point.

In the control section 40 of the present exemplary embodiment, a second threshold value is obtained in advance from the differential values obtained from the correspondence relationship between the contact surface area and the movement amount for a breast of the predetermined firmness (for example, a standard firmness). When the differential values are equal to or greater than the second threshold value, the pressing pressure (first pressing pattern) for cases in which the breast is firmer than the predetermined firmness is set. Namely, the second threshold value is a threshold value corresponding to the predetermined firmness of a breast. When setting the second threshold value and the first threshold value, these may be set based on a breast having substantially the same firmness. The same applies to a third threshold value described below.

Thus, negative determination is made at step S208 when the movement amount has not reached the predetermined movement amount, and a standby state is adopted while moving of the upper press member 28 is continued.

However, affirmative determination is made at step S208 when the movement amount reaches the predetermined movement amount, and processing transitions to step S210. At step S210, as described above, the control section 40 calculates the differential value as the amount of change.

Next, at step S212, determination is made as to whether or not the calculated differential value is equal to or greater than the second threshold value (differential values≥second threshold value). Affirmative determination is made when the differential value is equal to or greater than the second threshold value, and processing transitions to step S214. Cases in which affirmative determination is made at step S212 are cases in which the breast of the subject is firmer than the predetermined firmness.

Thus, at step S214, the control section 40 starts pressing with the first pressing pattern, and then processing transitions to step S218.

Negative determination is made at step S212 when the differential value is less than the second threshold value, and processing transitions to step S216. Cases in which negative determination is made at step S212 are cases in which the breast of the subject is softer than the predetermined firmness.

Thus, at step S216, the control section 40 starts pressing with the second pressing pattern, and then processing transitions to step S218.

At step S218 and S220, similar processing is performed to that of respective steps S112 and S114 in the image processing of the first exemplary embodiment (see FIG. 7), and the present image processing is ended after capturing a radiographic image at step S220.

A method to compare the amount of change in contact surface area with the second threshold value may, as explained above, be a method of calculating differential values plural times at each of the detection points and comparing these against the second threshold value each time, however, there is no limitation thereto. Another example is a method in which an average is taken for plural differential values, and the average then compared with the second threshold value. Another example that may be employed is to take, as the differential value, a ratio of the movement amount of the upper press member 28 from detection start to the predetermined movement amount to the amount of change in contact surface area, and compare this differential value against the second threshold value. Another example that may be employed is to perform a comparison of the amount of change in contact surface area from the detection start to the predetermined movement amount against the second threshold value. In this case, the amount of change in contact surface area of a breast of the predetermined firmness (for example, the standard firmness) may be acquired.

As a variation of the present exemplary embodiment, at steps S214 and S216, the upper pressing pressure (first pressing pressure) may be made equal to or lower than the lower pressing pressure (second pressing pressure) in the first pressing pattern, and the upper pressing pressure (first pressing pressure) may be made larger than the lower pressing pressure (second pressing pressure) in the second pressing pattern.

Third Exemplary Embodiment

In the present exemplary embodiment, explanation follows regarding a case in which the first pressing pressure of the upper press member 28 and the second pressing pressure of the lower press member 30 are set using the pressing pressure on the breast, and the contact surface area of breast contacting the lower press member 30.

As explained in the second exemplary embodiment, the manner of extension differs according to the firmness of the breast, and the firmer the breast, the more difficult it is to extend the breast, and the more difficult it is to increase the contact surface area. Therefore, in the present exemplary embodiment, the first pressing pressure of the upper press member 28 and the second pressing pressure of the lower press member 30 are set using the pressing pressure instead of the movement amount used in the second exemplary embodiment.

Figure 16:
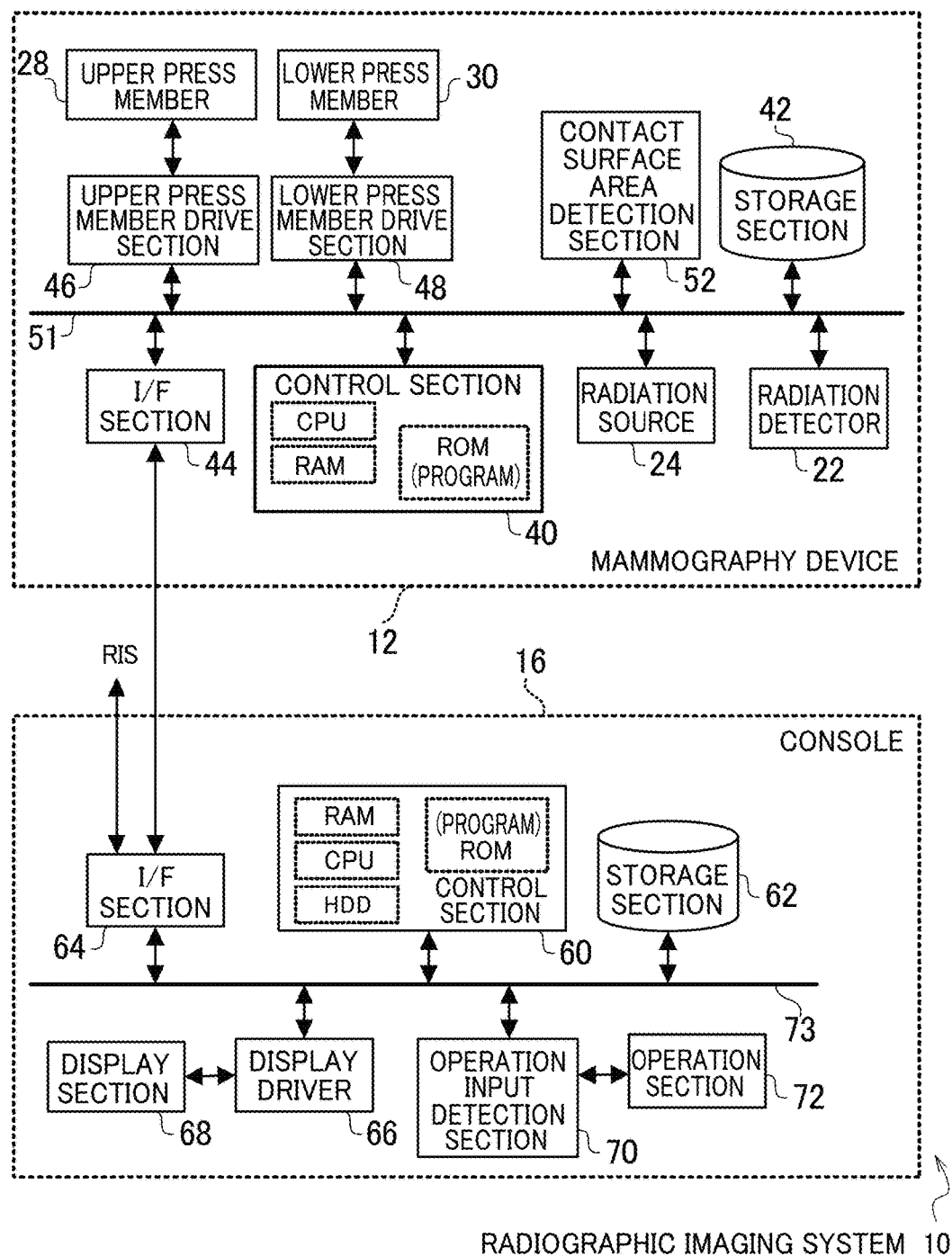
FIG. 16 is a block diagram illustrating an electrical configuration of a mammography apparatus and console of a third exemplary embodiment.

FIG. 16 is a block diagram illustrating a configuration of an electrical system of the mammography apparatus 12 and the console 16 according to the present exemplary embodiment.

As illustrated in FIG. 16, the mammography apparatus 12 of the present exemplary embodiment differs from the mammography apparatus 12 of the first exemplary embodiment (see FIG. 5) in being equipped with a contact surface area detection section 52. The mammography apparatus 12 of the present exemplary embodiment also differs from the mammography apparatus 12 of the second exemplary embodiment (see FIG. 9) in not being equipped with a movement amount detection section 50.

Figure 17:
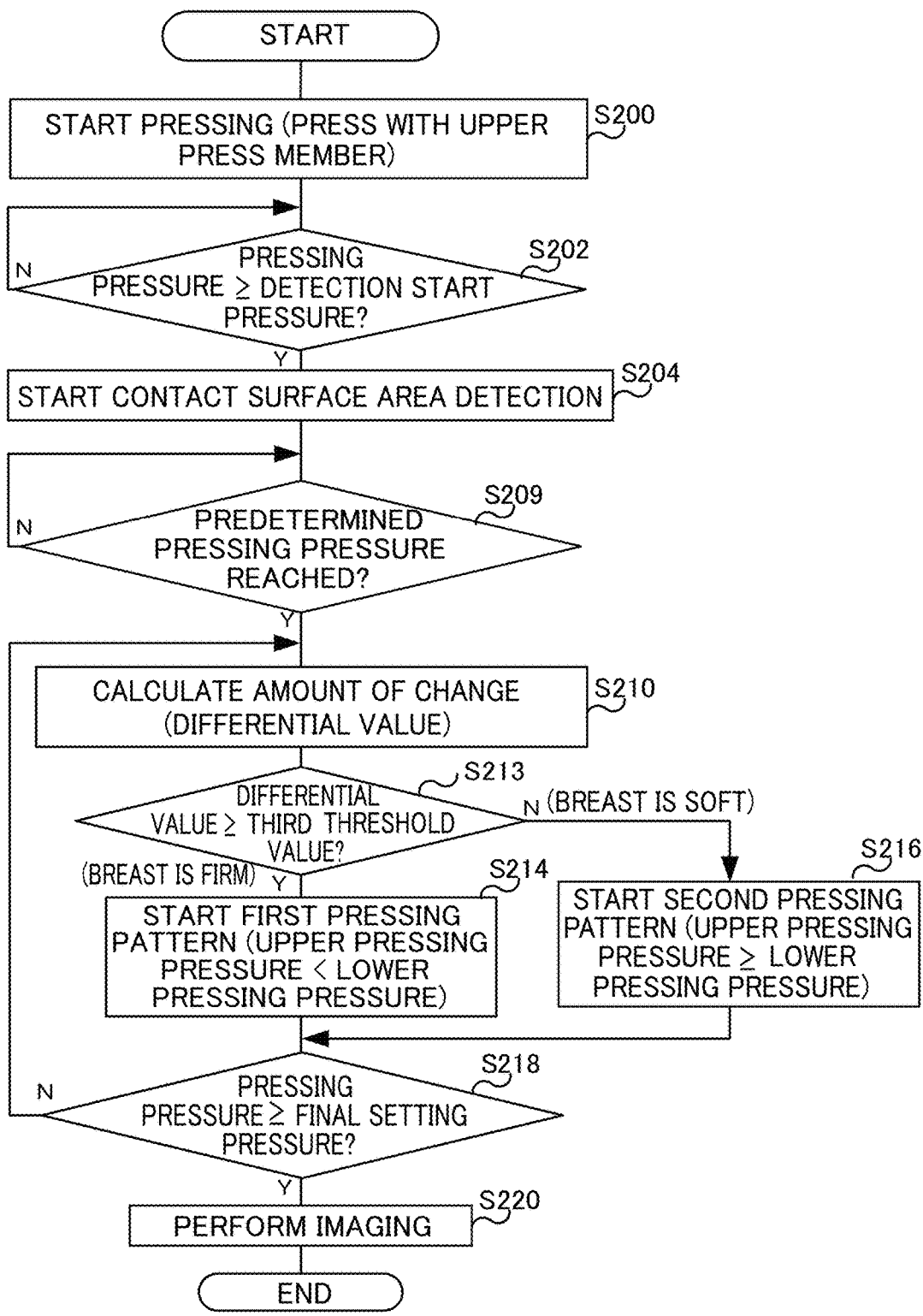
FIG. 17 is a flowchart illustrating a flow of imaging processing executed by a control section of a mammography apparatus of the third exemplary embodiment.

Explanation follows regarding image processing executed by the mammography apparatus 12 of the present exemplary embodiment. FIG. 17 is a flowchart illustrating an example of flow of image processing executed by a control section 40 of the mammography apparatus 12.

The image processing of the present exemplary embodiment is similar to the image processing of the second exemplary embodiment (see FIG. 13) except in that steps S206 and S208 are omitted, and steps S209 and S213 are provided instead of the steps S208 and S212. Detailed explanation of similar processing is omitted.

In the present exemplary embodiment, at step S204, the control section 40 starts detecting the contact surface area using the contact surface area detection section 52, and then transitions processing to step S209.

At step S209, the control section 40 determines whether or not the pressing pressure of the upper press member 28 reaches a predetermined pressing pressure (for example, an initial setting pressure). The predetermined pressing pressure here is a pressing pressure corresponding to the predetermined movement amount of the second exemplary embodiment.

In the mammography apparatus 12 of the present exemplary embodiment, the first pressing pressure of the upper press member 28 and the second pressing pressure of the lower press member 30 are set using the pressing pressure and the contact surface area over the period up to pressing the breast with the upper press member 28 at the predetermined pressing pressure.

Figure 18:
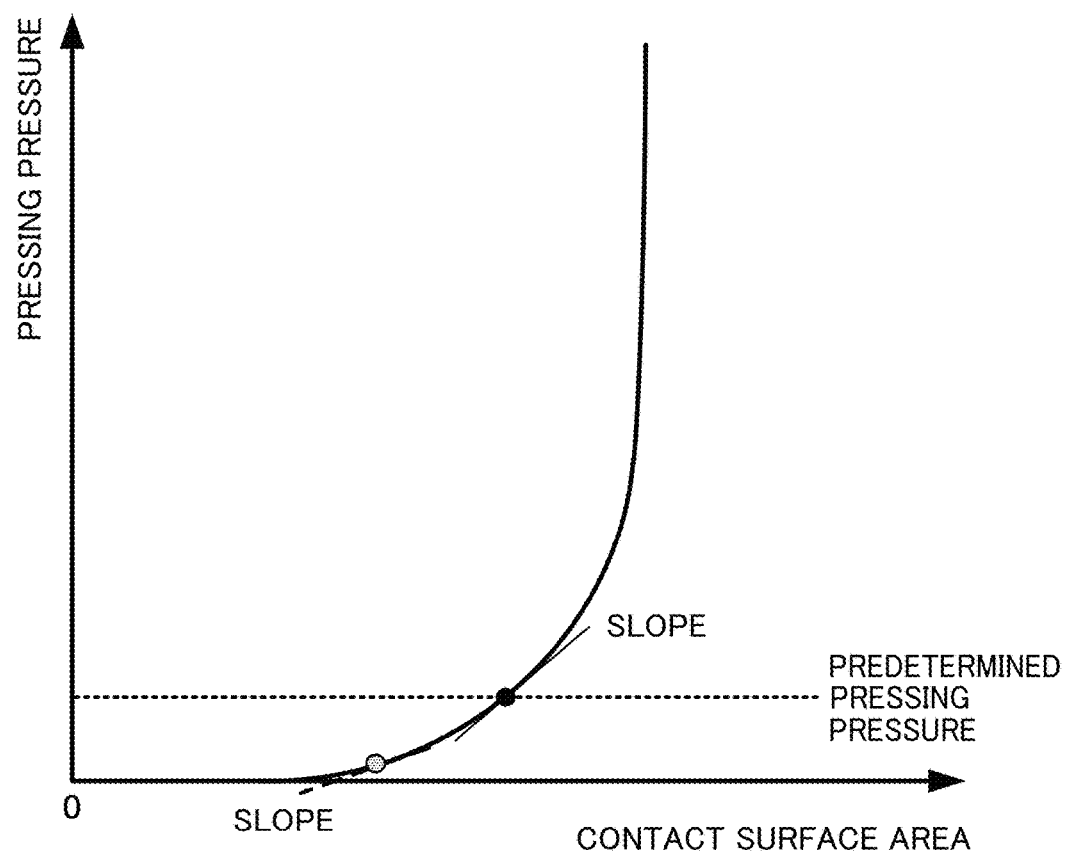
FIG. 18 is a graph illustrating an example of a correspondence relationship between breast contact surface area and pressing pressure on a breast.
Figure 19:
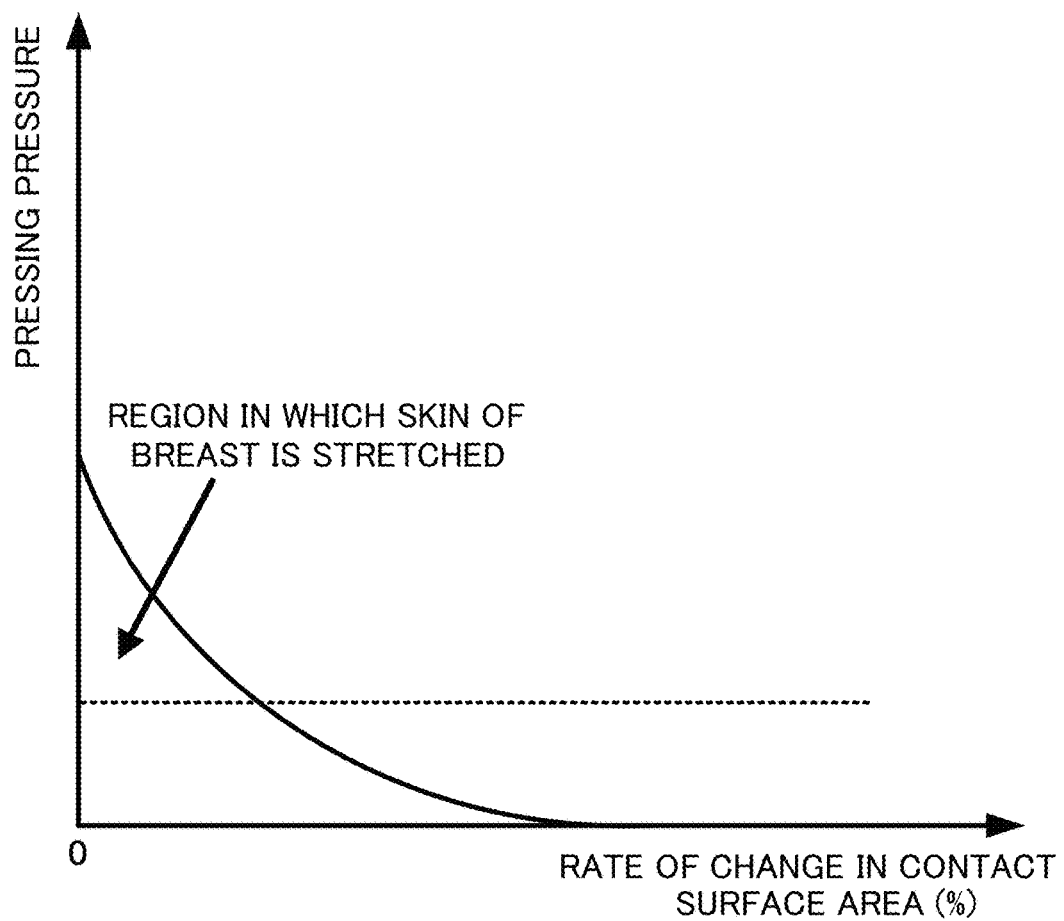
FIG. 19 is a graph illustrating an example of a correspondence relationship between rate of change in breast contact surface area and pressing pressure on a breast.

FIG. 18 is a graph illustrating an example of a correspondence relationship between the above contact surface area and the above pressing pressure. FIG. 19 is a graph illustrating an example of a correspondence relationship between the rate of change in contact surface area and the pressing pressure. In FIG. 19, similarly to in FIG. 15, the rate of change in contact surface area is derived by (the currently detected value of contact surface area−the immediately previously detected value of contact surface area)/the immediately previously detected contact surface area×100(%).

As illustrated in FIG. 18, the correspondence relationship between the contact surface area and the pressing pressure is analogous to the correspondence relationship between the contact surface area and the movement amount explained in the second exemplary embodiment (see FIG. 14). Further, as illustrated in FIG. 19, the correspondence relationship between the rate of change in contact surface area and the pressing pressure is analogous to the correspondence relationship between the contact surface area and the movement amount explained in the second exemplary embodiment (see FIG. 15). Note that since pressing pressure escapes when the breast is spread out and the contact surface area becomes large, the correspondence relationship between contact surface area or the rate of change in contact surface area and the pressing pressure is a steeper graph than the correspondence relationship between the contact surface area and the movement amount.

In the present exemplary embodiment, a correspondence relationship between the contact surface area and the pressing pressure over the period from starting of detection of the contact surface area up to the pressing pressure on the breast reaching the predetermined pressing pressure, as illustrated in FIG. 18, is obtained in advance. Then, by using the amount of change in contact surface area, specifically by using the differential values of the graph illustrated in FIG. 18, determination is made as to whether or not extension of the breast is difficult and whether or not increasing the contact surface area is difficult. The differential values in the graph illustrated in FIG. 18 are illustrated as the slopes of the graph at each of the detection points.

The control section 40 of the present exemplary embodiment obtains in advance the third threshold value based on the differential values obtained from the correspondence relationship between the contact surface area and the pressing pressure for a breast of the predetermined firmness (for example, the standard firmness), and sets the pressing pressure (the first pressing pattern) in cases in which the differential value is equal to or greater than the third threshold value, these being cases in which the breast is firmer than the predetermined firmness. Namely, the third threshold value is a threshold value corresponding to the predetermined firmness of a breast. When setting the third threshold value and the second threshold value, a breast having substantially the same firmness may be employed in the setting. Moreover, when setting the third threshold value, the first threshold value, and the second threshold value, a breast having substantially the same firmness may be employed in the setting.

Negative determination is made at step S209 when the pressing pressure on the breast has not reached the predetermined pressing pressure, and a standby state is adopted while moving of the upper press member 28 is continued.

However, affirmative determination is made at step S209 when the pressing pressure on the breast has reached the predetermined pressing pressure, and processing transitions to step S210.

At step S210, as described above, the control section 40 calculates the differential value as the amount of change and then transitions processing to step S213.

At step S213, determination is made as to whether or not the calculated differential value is equal to or greater than the third threshold value (differential value≥third threshold value). Affirmative determination is made in cases in which the differential value is equal to or greater than the third threshold value, and processing transitions to step S214. However, negative determination is made at step S212 when the differential value is less than the third threshold value, and processing transitions to step S216.

The processing of steps S214 to S220 is similar to the respective processing of steps 214 to S220 of the second exemplary embodiment (see FIG. 13).

The method of comparing the amount of change in contact surface area to the third threshold value is, as explained above, a method in which differential values are computed plural times at each of the detection points, and a comparison is made every time with the third threshold value, however, there is no limitation thereto. Another example of a method is to take an average of plural differential values, and to compare the average with the third threshold value. Another example that may be employed is to take, as the above differential value, a ratio of the pressing pressure of the upper press member 28 to the amount of change in contact surface area from the start of detection until reaching the predetermined pressing pressure, and to compare this differential value against the third threshold value. Another example that may be employed is to make a direct comparison between the amount of change in contact surface area from the start of detection until the predetermined pressing pressure, against the third threshold value. In this case, the amount of change in contact surface area may be acquired for a breast having the predetermined firmness (for example, the standard firmness).

As a variation of the present exemplary embodiment, at steps S214 and S216, the upper pressing pressure (first pressing pressure) may be equal to or lower than the lower pressing pressure (second pressing pressure) in the first pressing pattern, and the upper pressing pressure (first pressing pressure) may be larger than the lower pressing pressure (second pressing pressure) in the second pressing pattern.

As explained above, the mammography apparatus 12 in each of the exemplary embodiments is equipped with the imaging table 26 housing the radiation detector 22 that detects the radiation R after passing through the breast of the subject, the upper press member 28 that functions as a first press member that presses the breast downward from above when detecting the radiation R with the radiation detector 22, and the lower press member 30 that is provided facing the upper press member 28 and that functions as a second press member that presses the breast upward from below, wherein the end portion of the lower press member 30 on the side of the chest wall of the subject is supported by the imaging table 26. In the mammography apparatus 12 of each of the exemplary embodiments, when the breast is being pressed by the lower press member 30, the far side end portion of the lower press member 30 that is opposite to the chest wall side end portion is moved in the direction separating away from the imaging table 26.

Moreover, the control section 40 of the mammography apparatus 12 functions as a controller that effects control such that, when the breast is firmer than a predetermined firmness, the pressing pressure for pressing the breast with the lower press member 30 is controlled so as to be larger than the pressing pressure for pressing the breast with the upper press member 28.

Moreover, the control section 40 of the mammography apparatus 12 of each of the exemplary embodiments functions as a controller that sets the first pressing pressure of the upper press member 28 and the second pressing pressure of the lower press member 30 based on at least two factors selected from: the pressing pressures pressing the breast with the upper press member 28 and the lower press member 30; the contact surface area of the breast with at least one of the upper press member 28 or the lower press member 30; and the movement amount of at least one of the upper press member 28 and the low press member 30 that has moved to press the breast. The control section 40 of the mammography apparatus 12 in each of the exemplary embodiments accordingly functions as an estimator section that estimates the firmness of the breast of the subject.

Thus, in the mammography apparatus 12 of each of the exemplary embodiments, pressing is performed in accordance with the shape of the breast, because the end portion of the lower press member 30 at the chest wall side of the subject is supported by the imaging table 26, and the pressing of the breast is performed by moving the support portion 33 in a direction separating away from the imaging face 27 while the fixed portion 30B of the lower press member 30 remains fixed.

Accordingly, the mammography apparatus 12 in each of the exemplary embodiments is able to effectively reduce pain in the breast arising due to pressing.

Moreover, in the mammography apparatus 12 of each of the exemplary embodiments, the breast can be pressed according to the firmness of the breast because the second pressing pressure with the lower press member 30 being larger than the first pressing pressure with the upper press member 28 in cases in which the firmness of the breast is firmer than the predetermined firmness.

Accordingly, the mammography apparatus 12 of each of the exemplary embodiments is able to effectively reduce the pain on the breast due to pressing.

In the mammography apparatus 12 of the first exemplary embodiment, the configuration of the mammography apparatus 12 can be made more simple compared to that of the mammography apparatus 12 in the second and third exemplary embodiment, since the contact surface area detection section 52 does not need to be provided.

Each of the above exemplary embodiments may be combined. For example, with respect to the firmness of breast, final determination may be made as to whether or not the breast is firmer than the predetermined firmness based on a first result using the pressing pressure on the breast and the movement amount, as in the first exemplary embodiment, and based on a second result using the movement amount and the contact surface area, as in the second exemplary embodiment. Then, the first pressing pressure of the upper press member 28 and the second pressing pressure of the lower press member 30 may be set according to the determination result. In this case, for example, the final determination may be that the firmness of the breast is firmer than the predetermined firmness when both the first result and the second result have determined that the breast is firmer than the predetermined firmness, and otherwise, the final determination may be that the firmness of the breast is softer than the predetermined firmness in other cases.

Moreover, in each of the exemplary embodiments, a single respective threshold value (any one of the first threshold value to the third threshold value) is employed to determine whether or not the breast is firmer than the predetermined firmness, however, there is no limitation thereto. In each of the exemplary embodiments, two threshold values may be provided, and determination may be made as to whether or not the breast is firmer than, substantially the same as (i.e., has a standard firmness), or softer than the predetermined firmness. In this case, the second pressing pressure with the lower press member 30 may be set larger than the first pressing pressure with the upper press member 28 when the breast is firmer than the predetermined firmness, the second pressing pressure with the lower press member 30 may be set substantially the same as the first pressing pressure with the upper press member 28 when the breast is substantially the same firmness as the predetermined firmness, and the first pressing pressure with the upper press member 28 may be set larger than the second pressing pressure with the lower press member 30 when the breast is softer than the predetermined firmness.

Configurations in which two threshold values are provided in each exemplary embodiment are not limited to the above. For example, determination may be made that the breast is much firmer, the breast is slightly firmer, or the breast is softer than the predetermined firmness. In cases in which the breast is much firmer than the predetermined firmness, the second pressing pressure with the lower press member 30 may be set at a pressing pressure A that is larger than the first pressing pressure with the upper press member 28. In cases in which the breast is slightly firmer than the predetermined firmness, the second pressing pressure with the lower press member 30 may be set at a pressing pressure B that is larger than the first pressing pressure with the upper press member 28 and smaller than the pressing pressure A. In cases in which the breast is softer than the predetermined firmness, the first pressing pressure with the upper press member 28 may be set larger than the second pressing pressure with the lower press member 30.

Obviously, in the comparison of the calculated values in each of the present exemplary embodiments (the amount of change in FIG. 13 and FIG. 17, or the movement amount in FIG. 7) with the first to third threshold values, the issue of how to treat the boundary is within the scope of the technology of the present disclosure. For example, in FIG. 13, pressing with the first pressing pattern is started when the amount of change is equal to or greater than the second threshold value, and pressing with the second pressing pattern is started when the amount of change is less than the second threshold value. However, pressing with the first pressing pattern may be started when the amount of change is larger than the second threshold value, and pressing with the second pressing pattern may be started when the differential value is the second threshold value or less. The same applies to FIG. 17.

In each of the exemplary embodiments, the control section 40 of the mammography apparatus 12 is configured to perform pressing of the breast using both the upper press member 28 and the lower press member 30, however, there is no limitation thereto. For example, when the breast is firmer than the predetermined firmness, the breast may be pressed only with the lower press member 30. Moreover, for example, when the breast is softer than the predetermined firmness, the breast may be pressed only with the upper press member 28. Moreover, for example, when the breast is substantially the same firmness as the predetermined firmness, the breast may be pressed with substantially the same pressing pressure by both the upper press member 28 and the lower press member 30.

Explanation has been given above in each of the exemplary embodiments of cases in which the control section 40 sets the pressing pressure on the breast according to the firmness of the breast, however, there is no limitation thereto. For example, information related to the setting and the firmness of the breast may be displayed on the display section 68 of the console 16 or the like, and a user viewing the display may set the pressing pressures on the breast with the upper press member 28 and the lower press member 30.

Moreover, explanation has been given above in each of the exemplary embodiments of cases in which the control section 40 of the mammography apparatus 12 functions as a control section of the present disclosure, however, there is no limitation thereto. The function as the control section may be given to the control section 60 of the console 16.

Moreover, explanation has been given above in each of the exemplary embodiments of cases in which the mammography apparatus 12 is an apparatus capable of imaging the left and right breasts of a subject separately in a state in which the upper body of the subject is upright, however, the mammography apparatus is not limited thereto. For example, application may be made to a mammography apparatus that captures radiographic images of a pressed state of the breast of a subject lying down. In such cases, the "upper side (above)" described in the detailed description should be read as the head (cranio) side of the subject, and the "lower side (below)" described in the detailed description should be read as the foot (caudal) side of the subject.

There are no particular limitations to the radiation R employed for capturing radiographic images, and X-rays or gamma rays may be suitably employed.

Configuration and operation of the radiographic imaging system 10, the mammography apparatus 12, and the console 16 explained in the exemplary embodiments are merely examples, and obviously may be varied according to circumstances, within a range not departing from the scope and the spirit of the present disclosure.

What is claimed is:

1. A mammography apparatus comprising:
    an imaging table housing a radiation detector that detects radiation that has passed through a breast of a subject;
    a first press member that presses the breast downward from above in a case in which radiation is being detected by the radiation detector;
    a second press member that is provided facing the first press member and that presses the breast upward from below, wherein an end portion of the second press member at a chest wall side of the subject is supported by the imaging table; and
    a control section that is configured to effect control of setting a first pressing pressure for pressing the breast with the first press member and a second pressing pressure for pressing the breast with the second press member, based on at least two factors selected from the group consisting of: a detected pressing pressure of the first press member pressing the breast a contact surface area of the breast with at least one of the first press member or the second press member; and a movement amount by which at least one of the first press member or the second press member has moved to press the breast,
    wherein the control section is configured to set the first pressing pressure and the second pressing pressure so as to have different relative proportions, based on a result of determining whether or not the movement amount corresponding to the detected pressing pressure is less than a first threshold value.

2. The mammography apparatus of claim 1, wherein an end portion of the second press member at the far side that is opposite to the end portion at the chest wall side is moved in a direction separating away from the imaging table in a case in which the breast is being pressed by the second press member.

3. The mammography apparatus of claim 1, wherein the control section is configured to set the second pressing pressure to be larger than the first pressing pressure, or to move only the second press member, in a case in which it is determined that the movement amount corresponding to the detected pressing pressure is less than the first threshold value.

4. The mammography apparatus of claim 1, wherein the second press member is supported by the imaging table so as to be capable of swinging, or is supported by being fixed.

5. The mammography apparatus of claim 1, wherein the second press member comprises a film-shaped member.

6. A mammography apparatus, comprising:
    an imaging table housing a radiation detector that detects radiation that has passed through a breast of a subject;
    a first press member that presses the breast downward from above in a case in which radiation is being detected by the radiation detector;

a second press member that is provided facing the first press member and that presses the breast upward from below, wherein an end portion of the second press member at a chest wall side of the subject is supported by the imaging table; and a control section that is configured to effect control of setting a first pressing pressure for pressing the breast with the first press member and a second pressing pressure for pressing the breast with the second press member, based on at least two factors selected from the group consisting of: a detected pressing pressure of the first press member pressing the breast a contact surface area of the breast with at least one of the first press member or the second press member; and a movement amount by which at least one of the first press member or the second press member has moved to press the breast, wherein the control section is configured to set the first pressing pressure and the second pressing pressure so as to have different relative proportions, based on a result of determining whether or not an amount of change in the contact surface area, over a period until a movement amount of the first press member reaches a predetermined movement amount, is larger than a predetermined second threshold value that has been set according to a predetermined firmness.

7. The mammography apparatus of claim 6, wherein the control section is configured to set the second pressing pressure to be larger than the first pressing pressure, or to move only the second press member, in a case in which it is determined that the amount of change in the contact surface area is larger than the second threshold value.

8. A mammography apparatus, comprising:
an imaging table housing a radiation detector that detects radiation that has passed through a breast of a subject;
a first press member that presses the breast downward from above in a case in which radiation is being detected by the radiation detector;
a second press member that is provided facing the first press member and that presses the breast upward from below, wherein an end portion of the second press member at a chest wall side of the subject is supported by the imaging table; and
a control section that is configured to effect control of setting a first pressing pressure for pressing the breast with the first press member and a second pressing pressure for pressing the breast with the second press member, based on at least two factors selected from the group consisting of: a detected pressing pressure of the first press member pressing the breast a contact surface area of the breast with at least one of the first press member or the second press member; and a movement amount by which at least one of the first press member or the second press member has moved to press the breast, wherein the control section is configured to set the first pressing pressure and the second pressing pressure so as to have different relative proportions, based on a result of determining whether or not an amount of change in the contact surface area, over a period until the detected pressing pressure due to movement of the first press member has reached a predetermined pressing pressure, is larger than a predetermined third threshold value that has been set according to the predetermined firmness.

9. The mammography apparatus of claim 8, wherein the control section is configured to set the second pressing pressure to be larger than the first pressing pressure, or to move only the second press member, in a case in which it is determined that the amount of change in contact surface area is larger than the third threshold value.

10. A control device for controlling a mammography apparatus including an imaging table housing a radiation detector that detects radiation that has passed through the breast of a subject, a first press member that presses the breast downward from above in a case in which radiation is being detected by the radiation detector, and a second press member that is provided facing the first press member and that presses the breast upward from below, wherein an end portion of the second press member at a chest wall side of the subject is supported by the imaging table, the control device comprising a control section that is configured to set a first pressing pressure for pressing the breast with the first press member and a second pressing pressure for pressing the breast with the second press member, based on at least two factors selected from the group consisting of: a detected pressing pressure of the first press member pressing the breast; a contact surface area of the breast with at least one of the first press member or the second press member; and a movement amount by which at least one of the first press member or the second press member has moved to press the breast, and is configured to set the first pressing pressure and the second pressing pressure so as to have different relative proportions, based on a result of determining whether or not the movement amount corresponding to the detected pressing pressure is less than a first threshold value.

11. The control device of claim 10, wherein the control section is configured to set the second pressing pressure to be larger than the first pressing pressure.

12. A control method of a mammography apparatus including an imaging table housing a radiation detector that detects radiation that has passed through the breast of a subject, a first press member that presses the breast downward from above in a case in which radiation is being detected by the radiation detector, and a second press member that is provided facing the first press member and that presses the breast upward from below, wherein an end portion of the second press member at a chest wall side of the subject is supported by the imaging table, the control method causing a computer to execute processing comprising:
setting a first pressing pressure for pressing the breast with the first press member and a second pressing pressure for pressing the breast with the second press member, based on at least two factors selected from the group consisting of: a detected pressing pressure of the first press member pressing the breast; a contact surface area of the breast with at least one of the first press member or the second press member; and a movement amount by which at least one of the first press member or the second press member has moved to press the breast, and
setting the first pressing pressure and the second pressing pressure so as to have different relative proportions, based on a result of determining whether or not the movement amount corresponding to the detected pressing pressure is less than a first threshold value.

13. A non-transitory storage medium storing a program that causes a computer to execute control processing of a mammography apparatus including an imaging table housing a radiation detector that detects radiation that has passed through the breast of a subject, a first press member that presses the breast downward from above in a case in which radiation is being detected by the radiation detector, and a second press member that is provided facing toward the first press member and that presses the breast upward from below, wherein an end portion of the second press member at a chest wall side of the subject is supported by the imaging table, the control processing comprising:

setting a first pressing pressure for pressing the breast with the first press member and a second pressing pressure for pressing the breast with the second press member, based on at least two factors selected from the group consisting of: a detected pressing pressure of the first press member pressing the breast; a contact surface area of the breast with at least one of the first press member or the second press member; and a movement amount by which at least one of the first press member or the second press member has moved to press the breast, and setting the first pressing pressure and the second pressing pressure so as to have different relative proportions, based on a result of determining whether or not the movement amount corresponding to the detected pressing pressure is less than a first threshold value.

\* \* \* \* \*